US010376421B2

(12) United States Patent
Coe et al.

(10) Patent No.: US 10,376,421 B2
(45) Date of Patent: Aug. 13, 2019

(54) METHOD FOR DEFORMING A WEB

(71) Applicant: The Procter & Gamble Company, Cincinnati, OH (US)

(72) Inventors: Richard George Coe, Cincinnati, OH (US); Kevin Gerard Muhs, Hamilton, OH (US); Robert Karl Isburgh, Loveland, OH (US); Rong Deng, Mason, OH (US); Amit Kumar Kaushik, West Chester, OH (US); Mathias Johannes Hilpert, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 400 days.

(21) Appl. No.: 14/994,249

(22) Filed: Jan. 13, 2016

(65) Prior Publication Data

US 2016/0235590 A1    Aug. 18, 2016

Related U.S. Application Data

(60) Provisional application No. 62/116,914, filed on Feb. 17, 2015.

(51) Int. Cl.
| | |
|---|---|
| *A61F 13/15* | (2006.01) |
| *B29C 69/00* | (2006.01) |
| *A61F 13/511* | (2006.01) |
| *B29L 31/48* | (2006.01) |

(52) U.S. Cl.
CPC .. *A61F 13/15585* (2013.01); *A61F 13/15707* (2013.01); *A61F 13/15804* (2013.01); *A61F 13/511* (2013.01); *B29C 69/001* (2013.01); *B29L 2031/4878* (2013.01)

(58) Field of Classification Search
CPC .......... A61F 13/15585; A61F 13/15707; A61F 13/15804; A61F 13/511; B29C 69/001; B29L 2031/4878
See application file for complete search history.

(56) References Cited

U.S. PATENT DOCUMENTS

| | | | |
|---|---|---|---|
| 4,767,586 A * | 8/1988 | Radwanski | D21F 9/00 |
| | | | 264/112 |
| 2004/0015145 A1 | 1/2004 | Miura et al. | |
| 2004/0127875 A1 | 7/2004 | Hammons et al. | |
| 2015/0313766 A1* | 11/2015 | Miao | A61F 13/475 |
| | | | 604/385.101 |

FOREIGN PATENT DOCUMENTS

WO    WO 00/59438 A1    10/2000

OTHER PUBLICATIONS

PCT International Search Report, dated Jun. 22, 2016, 101 pages.

* cited by examiner

*Primary Examiner* — Anthony Calandra
*Assistant Examiner* — Jamel M Nelson
(74) *Attorney, Agent, or Firm* — George H. Leal; Andrew J. Hagerty

(57) ABSTRACT

The present invention is directed to methods for deforming a web comprising the steps of supplying a precursor web; weakening the precursor web at a plurality of locations to create a plurality of weakened, melt-stabilized locations in precursor web; and forming a plurality of first features and a plurality of second features throughout the first and second layers of the web in the z-direction, wherein the plurality of first and second features are formed simultaneously.

20 Claims, 12 Drawing Sheets

METHOD FOR DEFORMING A WEB

FIELD OF THE INVENTION

The present invention relates to methods and apparatuses for deforming a web.

BACKGROUND OF THE INVENTION

Laminate webs containing a film layer and/or a fibrous nonwoven layer are well known in the art. Three-dimensionally deformed laminate webs are utilized in a wide variety of industrial and consumer products. For example, nonwoven webs are often laminated with polymer films such that they are useful as materials in disposable products such as topsheets on disposable absorbent articles.

Apertured webs are known for use in disposable absorbent articles such as feminine hygiene articles including sanitary napkins, and disposable diapers and the like. Such articles typically have a fluid pervious topsheet, a fluid impervious breathable backsheet, and an absorbent core disposed between the topsheet and the backsheet. Apertured webs can be made to form a fluid pervious topsheet and/or the fluid impervious breathable backsheet in absorbent articles. Webs having loops or tufts are also desirable as such webs have a bulky texture and/or softness.

Designers of absorbent articles are faced with the challenge of designing articles that provide for healthy skin in all regions of the wearer's crotch. In some instances, the benefit of providing for skin health in one region is obtained at the expense of decreased skin health in another region. Designs that apply a uniform approach across the entire absorbent article may not provide for satisfactory skin health and fluid acquisition throughout the entire crotch region. Furthermore, skin health and the feeling of wetness can impact how comfortable the absorbent article is to wear.

Meanwhile, various fluid handling demands on different portions of an absorbent article, and different physical interactions between portions of an absorbent article and portions of a wearer's body create unique needs for different regions of the topsheet which may be met by forming different structures in different regions. In addition, expectation of enhanced perceptions of functionalities of absorbent articles such as absorbency and breathability also creates needs for structural features in predetermined regions of the topsheet. To meet such needs, one layer of the web, or multiple layers of the web may be deformed to form different structures in predetermined regions.

In many cases to provide best functionality and enhanced perceptions of absorbent articles, several structures may be formed in a continuous process comprising multiple unit steps. Formation of features in a web in a different sequence may cause weakening of the web structure, thereby causing tearing during the manufacturing process or in use. Further, separation of unit steps of structure formations may increase the possibility that some or many structures closely co-located in a web formed in different unit steps overlap.

A need exists for processes and apparatuses that will allow a web to be deformed to have structures in different regions via single unit operation. Especially, a need exists for processes and apparatuses that are capable of deforming a web where at least one of structures is formed in one layer or limited numbers of layers of the web while other structures are formed through the entire web in z-dimension.

SUMMARY OF THE INVENTION

The present invention is directed to a process for deforming a web comprising the steps of providing a precursor web comprising a first layer and a second layer, weakening the precursor web at a plurality of locations in a first area where both the first layer and second layer exist to create a plurality of weakened, melt-stabilized locations, and simultaneously forming a plurality of first features coincident with the plurality of weakened, melt-stabilized locations in the first area and a plurality of second features in a second area of the precursor web where the second layer does not exist. The processes and apparatuses of the present invention can, in certain non-limiting embodiments, be configured for deforming a multilayer web in a single nip. In one embodiment, a plurality of first features and a plurality of second features are formed by feeding the web in a machine direction into a nip that is formed between two intermeshing rolls comprising a first roll comprising a first region comprising a plurality of first forming elements wherein the plurality of first forming elements comprise a plurality of circumferentially-extending ridges separated by grooves, and a second region comprising a plurality of circumferentially-extending ridges separated by grooves on its surface; and a second roll comprising a first region comprising a plurality of circumferentially-extending ridges separated by grooves and a second region comprising a plurality of second forming elements on its surface.

The present invention is also directed to a process for deforming a web comprising the steps of providing a precursor web comprising a first layer and a second layer, and forming a plurality of first features in a first area of the precursor web where both the first and second layers exist and a plurality of second features in a second area of the precursor web where the second layer does not exist.

When the web is fed into the nip, at least some of the plurality of first forming elements in the first region of the first roll and at least some of ridges in the first region of the second roll are intermeshed to from the plurality of first features. The second forming elements of the second roll and the optional third forming elements of the first roll form the plurality of second features and the plurality of optional third features, respectively.

BRIEF DESCRIPTION OF THE DRAWINGS

The following detailed description will be more fully understood in view of the drawings in which.

Figure 1A:
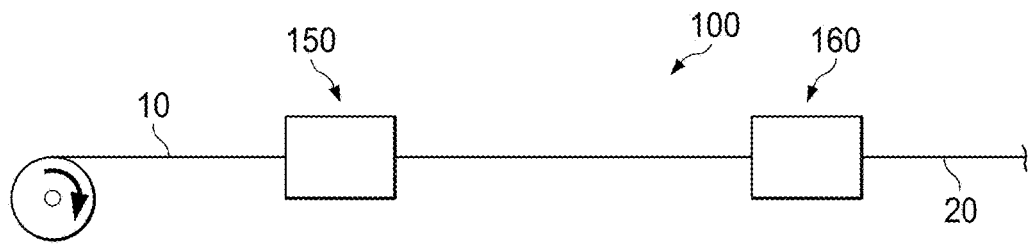
FIG. 1A is a schematic side view of one embodiment of a method and apparatus for deforming a web according to the present invention.

The embodiments shown in the drawings are illustrative in nature and are not intended to be limiting of the invention defined by the claims. Moreover, the features of the invention will be more fully apparent and understood in view of the detailed description.

DETAILED DESCRIPTION

The term "absorbent article" includes disposable articles such as sanitary napkins, panty liners, tampons, interlabial devices, wound dressings, diapers, adult incontinence articles, wipes, and the like. Still further, the absorbent members produced by the processes and apparatuses disclosed herein can find utility in other webs such as scouring pads, dry-mop pads (such as SWIFFER® pads), and the like. At least some of such absorbent articles are intended for the absorption of body liquids, such as menses or blood, vaginal discharges, urine, and feces. Wipes may be used to absorb body liquids, or may be used for other purposes, such as for cleaning surfaces. Various absorbent articles described above will typically comprise a liquid pervious topsheet, a liquid impervious backsheet joined to the topsheet, and an absorbent core between the topsheet and backsheet.

The term "absorbent core", as used herein, refers to the component of the absorbent article that is primarily responsible for storing liquids. As such, the absorbent core typically does not include the topsheet or backsheet of the absorbent article.

The term "absorbent member", as used herein, refers to the components of the absorbent article that typically provide one or more liquid handling functionality, e.g., liquid acquisition, liquid distribution, liquid transportation, liquid storage, etc. If the absorbent member comprises an absorbent core component, the absorbent member can comprise the entire absorbent core or only a portion of the absorbent core.

The term "absorbent structure", as used herein, refers to an arrangement of more than one absorbent component of an absorbent article.

The term "adjacent", as used herein, with reference to features, areas, or regions, means near or close to, and which need not be in contact with each other.

The term "aperture", as used herein, refers to a hole. The apertures can either be punched cleanly through the web so that the material surrounding the aperture lies in the same plane as the web prior to the formation of the aperture (a "two dimensional" aperture), or holes formed in which at least some of the material surrounding the opening is pushed out of the plane of the web. In the latter case, the apertures may resemble a protrusion or depression with an aperture therein, and may be referred to herein as a "three dimensional" aperture, a subset of apertures.

The term "component" of an absorbent article, as used herein, refers to an individual constituent of an absorbent article, such as a topsheet, acquisition layer, liquid handling layer, absorbent core or layers of absorbent cores, backsheets, and barriers such as barrier layers and barrier cuffs.

The term "cross-machine direction" or "CD" means the path that is perpendicular to the machine direction in the plane of the web.

The term "deformable material", as used herein, is a material which is capable of changing its shape or density in response to applied stresses or strains. Such deformable materials may be chemically homogeneous or heterogeneous, such as homopolymers and polymer blends, structurally homogeneous or heterogeneous, such as plain sheets or laminates, or any combination of such materials.

The term "discrete", as used herein, means distinct or unconnected. When the term "discrete" is used relative to forming elements on a forming member, it is meant that the distal (or radially outwardmost) ends of the forming elements are distinct or unconnected in all directions, including in the machine and cross-machine directions (even though bases of the forming elements may be formed into the same surface of a roll, for example).

The term "forming element(s)", as used herein, refers to any elements on the surface of a forming member that are capable of deforming a web. The term "forming element(s)" includes both continuous or non-discrete forming elements such as the ridges and grooves on ring rolls, and discrete forming elements such as teeth.

The term "intermixed", as used herein, refers to features that are distributed between other features over at least some portion of the surface of a component, in which the features differ from each other as described herein. The term "intermixed" comprises arrangements of features in which at least two of the closest features in any direction (including, but not limited to longitudinal, transverse, or diagonal) differ from each other as described herein, even though there may be a similar feature that is as close as, or closer to, a given feature in another direction.

The term "Interpenetrating SELF" and the acronym "IPS", as used herein, refers to a process that uses The Procter & Gamble Company's SELF technology (described below) to combine at least two layers or materials together. Tufts may be formed in both materials; or, the tuft of one material may burst through the other material. Interpenetrating SELF is described in greater detail in U.S. Pat. No. 7,648,752.

The term "joined to" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The term "joined to" encompasses configurations in which an element is secured to another element at selected locations, as well as configurations in which an element is completely secured to another element across the entire surface of one of the elements. The term "joined to" includes any known manner in which elements can be secured including, but not limited to mechanical entanglement.

The term "layer" is used herein to refer to an absorbent member whose primary dimension is X-Y, i.e., along its length (or longitudinal direction) and width (or transverse direction). It should be understood that the term "layer" is not necessarily limited to single layers or sheets of material. Thus the layer can comprise laminates or combinations of several sheets or webs of the requisite type of materials. Accordingly, the term "layer" includes the terms "layers" and "layered".

The term "machine direction" or "MD" means the path that material, such as a web, follows through a manufacturing process.

The term "male/female embossing" as used herein, refers to an embossing apparatus and process that involves the use of at least a pair of patterned rolls, wherein the first patterned roll comprises one or more projections or protrusions, and the second patterned roll comprises one or more recesses into which one or more of the projections of the first patterned roll mesh. The projections and recesses may be discrete embossing elements, and they may have matched or unmatched patterns. The term "male/female embossing", thus, excludes embossing processes that utilize the combination of a patterned roll against a flat anvil roll or deformable roll.

The term "macroscopic", as used herein, refers to structural features or elements that are readily visible and distinctly discernable to a human having 20/20 vision when the perpendicular distance between the viewer's eye and the web is about 12 inches (30 cm). Conversely, the term "microscopic" refers to such features that are not readily visible and distinctly discernable under such conditions.

The terms "mechanically impacting" or "mechanically deforming", may be used interchangeably herein, to refer to processes in which a mechanical force is exerted upon a material.

The term "Micro-SELF" is a process that is similar in apparatus and method to that of the SELF process defined herein. Micro-SELF teeth have different dimensions such that they are more conducive to forming tufts with openings on the leading and trailing edges. A process using micro-SELF to form tufts in a web substrate is disclosed in U.S. Patent application Publication No. US 2006/0286343A1.

The term "permanently deformed", as used herein, refers to the state of a deformable material whose shape or density has been permanently altered in response to applied stresses or strains.

The term "rib-like structure(s)", as used herein, refers to an embossment, debossment or a combination thereof which has a major axis and a minor axis. Preferably, the major axis is at least as long as the minor axis. The major axes of the rib-like structures are preferably oriented substantially perpendicular to the axis of applied elongation. Rib-like structures may have continuous side walls associated therewith, i.e., a continuous "transition zone," and may not exhibit rupturing of a web. Rib-like structures is understood to include tufts.

The terms "ring roll" or "ring rolling" refer to a process using deformation members comprising counter rotating rolls, intermeshing belts or intermeshing plates containing continuous ridges and grooves where intermeshing ridges (or projections) and grooves (or recesses) of deformation members engage and stretch a web interposed therebetween. For ring rolling, the deformation members can be arranged to stretch the web in the cross machine direction or the machine direction depending on the orientation of the ridges and grooves.

The term "rotary knife aperturing" (RKA) refers to a process and apparatus using intermeshing forming elements similar to those described herein with respect to SELF or micro-SELF forming elements. The RKA process differs from SELF or micro-SELF in that the SELF or micro-SELF forming elements which are relatively flat, elongated teeth have been modified to be pyramid shaped, elongated with at least six sides, the sides being substantially triangular and tapered to a point at the distal end. The RKA teeth can be sharpened to cut through as well as deform a web to produce an apertured web, or in some cases, a three-dimensionally apertured web, as disclosed in U.S. Patent Application Publication Nos. US 2005/0064137A1, US 2006/0087053A1, and US 2005/021753. In other respects such as tooth height, tooth spacing, pitch, depth of engagement, and other processing parameters, RKA and the RKA apparatus can be the same as described herein with respect to SELF or micro-SELF.

The terms "SELF" or "SELFing", refer to Procter & Gamble technology in which SELF stands for Structural Elastic Like Film. While the process was originally developed for deforming polymer film to have beneficial structural characteristics, it has been found that the SELFing process can be used to produce beneficial structures in other materials. Processes, apparatuses with SELF teeth, and patterns produced via SELF are illustrated and described in U.S. Pat. Nos. 5,518,801; 5,691,035; 5,723,087; 5,891,544; 5,916,663; 6,027,483; and 7,527,615.

The term "tuft", as used herein, refers to a particular type of protrusion. Tufts may have a tunnel-like configuration, and in some cases may be open at one or both of their ends.

The term "Z-dimension" refers to the dimension orthogonal to the length and width of a web. The Z-dimension usually corresponds to the thickness of the web.

I. Deformed Web.

The present inventions are directed to processes and apparatuses for deforming a web. Processes and apparatuses are disclosed that are capable of forming new structures in webs that provide the webs with additional properties. It should be understood that while the term "deformed web" is utilized herein, the object is to create components, such as absorbent members (or non-absorbent components), for absorbent articles from such deformed web. In such cases, the deformed web will be cut into individual components for absorbent articles. The deformed web can also be used in products other than absorbent articles including, but not limited to packaging materials and trash bags.

Structures which can be provided in webs and the components formed therefrom include features extending out of the plane of the web on at least one side thereof. In the case of webs used in absorbent articles, such structures may include those that provide a single portion of the web with at least one property (such as improved softness, fluid handling, or other properties) in a predetermined portion of the web.

The process can allow a precursor web comprising a first layer and a second layer to be simultaneously deformed in at least one first area where both the first and second layers exist, and at least one second area where the second layer does not exist.

The deformed web or precursor web comprises a first layer and a second layer each of which comprises any suitable deformable material. Such a suitable deformable material can be a woven, nonwoven, film, paper, tissue, knitted fabric, combination, composite or laminate of any of the foregoing materials.

As used herein, the term a "nonwoven" refers to a material having a structure of individual fibers or threads which are interlaid, but not in a repeating pattern as in a woven or knitted fabric, which do not typically have randomly oriented fibers. Nonwoven or fabrics have been formed from many processes, such as, for example, meltblowing, spunbonding, hydroentangling, airlaid, wetlaid, through-air-dried paper making processes, and bonded carded web processes, including carded thermal bonding. The woven, nonwoven, film, combination, or laminate can be made of any suitable materials including, but not limited to natural materials, synthetic materials, and combinations thereof. Suitable natural materials include, but are not limited to cellulose, cotton linters, bagasse, wool fibers, silk fibers, etc. In some embodiments, the web materials may be substantially free of cellulose, and/or exclude paper materials. In other embodiments, the methods described herein may be performed on cellulose-containing precursor materials.

As used herein, the term a "polymeric film" comprise thermoplastic polymers having characteristic rheological properties which depend on their composition and temperature. Below their glass transition temperature, such thermoplastic polymers can be hard, stiff, and/or brittle. Below the glass transition temperature, the molecules are in rigid, fixed positions. Above the glass transition temperature but below the melt temperature range, thermoplastic polymers exhibit viscoelasticity. In this temperature range, the thermoplastic material generally has a certain degree of crystallinity, and is generally flexible and to some degree deformable under a force. The deformability of such a thermoplastic is dependent on the rate of deformation, amount (dimensional quantity) of deformation, length of time it is deformed, and its temperature. In one embodiment, processes can be utilized to form materials comprising thermoplastic polymers, especially thermoplastic film, which are within this viscoelastic temperature range. Polymeric film can comprise a certain amount of ductility. Ductility, as used herein, is the amount of permanent, unrecoverable, plastic strain which occurs when a material is deformed, prior to failure (rupture, breakage, or separation) of the material. Materials that can be used as described herein can have a minimum ductility of at least about 10%, or at least about 50%, or at least about 100%, or at least about 200%. Polymeric film webs can include materials normally extruded or cast as films such as polyolefins, nylons, polyesters, and the like. Such films can be thermoplastic materials such as polyethylene, low density polyethylene, linear low density polyethylene, polypropylenes and copolymers and blends containing substantial fractions of these materials. Such films can be treated with surface modifying agents to impart hydrophilic or hydrophobic properties, such as imparting a lotus effect. As noted below, polymeric film can be textured or otherwise altered from a strictly flat, planar configuration.

In one non-limiting embodiment, the deformed web comprises a) a plurality of first features comprising apertures formed throughout the web in z-dimension in a firs area of the web where the first and second layers exist, and b) a plurality of second features formed in at least one second area of the web where the second layer does not exist. In case the web is a two-layer web, the second features are formed in the first layer only. In case the web is a three or more layer web, the second features may be formed through the entire layers exiting in the second area.

In another non-limiting embodiment, the deformed web further comprises a plurality of third features formed in at least one third area of the web where both the first and second layers exist. The first area and the third area may be distinctively separated each other, or overlap each other at least in part.

In some embodiments, the second features and/or the third features may be selected from the group consisting of one or more of the foregoing types of features. For example, the second and/or third features can comprise apertures, protrusions, or depressed areas (or "depressions"). The second features may be of a different type and/or have different properties or characteristics than the first features or the optional third features. The deformed web may further comprise fourth or more formed features. The fourth, or more features may comprise any of the types of features or have any of the properties described herein, and may differ from the first and second features in any such aspects.

The first features and second features may be of any suitable size. Typically, either the first features or the second features can be macroscopic. In some embodiments, the first features and the second features will both be macroscopic. The plan view area of the individual features may, in some embodiments of the web, be greater than or equal to about 0.5 mm$^2$, 1 mm$^2$, 5 mm$^2$, 10 mm$^2$, or 15 mm$^2$, or lie in any range between two of these numbers. The methods described herein can, however, be used to create first features and/or second features that are microscopic which have plan view areas less than 0.5 mm$^2$.

The second features and the optional third features, and other optional features may be of any suitable configuration. The features may be continuous and/or discrete. Suitable configurations for the features include, but are not limited to: ridges (continuous protrusions) and grooves (continuous depressions); tufts; columnar shapes; dome-shapes, tent-shapes, volcano-shapes; features having plan view configurations including circular, oval, hour-glass shaped, star shaped, polygonal, polygonal with rounded corners, and the like, and combinations thereof. Polygonal shapes include, but are not limited to rectangular (inclusive of square), triangular, hexagonal, or trapezoidal.

The first features and the second features may differ from each other in terms of one or more of the following properties: type, shape, size, aspect ratio, edge-to-edge spacing, height or depth, density, color, surface treatment (e.g., lotion, etc.), number of web layers within the features, and orientation (protruding from different sides of the web). The term "type", as used herein, refers to whether the feature is an aperture (a two dimensional aperture, or a three dimensional aperture), a protrusion (a tuft, or other kind of protrusion), or a depression. Two features will be considered to be different in type if one feature comprises one of these features listed (for example, a two dimensional aperture), and the other feature comprises another one of the listed features (for example, a three dimensional aperture). When the features are described as differing from each other in one of more of the properties listed above, it is meant to include those differences other than minor differences that are the result of variations within manufacturing tolerances. It should also be understood that although the web may have discrete thermal or adhesive bond sites therein, in some embodiments the features of interest imparted by this process herein do not include such bond sites.

In one embodiment, the first features are features selected from the group consisting of apertures, protrusions, depressions, tufts, and combinations thereof, and the second discrete feature are features selected from the group consisting of apertures, protrusions, depressions, tufts, and combinations thereof. In another embodiment, the first features are apertures and the second features are tufts.

The various types of deformed webs will be shown in conjunction with the descriptions of the apparatuses and processes used to form the same. These webs can be cut to form various components of products such as absorbent articles (such as topsheets, backsheets, acquisition layers, absorbent cores), packaging (such as flow wrap, shrink wrap, and polybags), trash bags, food wrap, wipes, facial tissue, toilet tissue, paper towels, and the like.

II. Processes and Apparatuses for Deforming Webs

It is desirable to design a process that enables better control over the formation of two or more sets of features. An approach for achieving better control over the formation of each set of features is provided here. The approach utilizes a single nip with two rolls comprising discrete male forming elements wherein at least one roll comprises two or more ridges. This approach may enable better control over the formation of each set of features in a single unit operation. This approach may enable the formation of multiple features in a single unit operation, which eliminates or mitigate the risks of overlapping of these features if they were formed in separate steps, and of misalignment or overlapping of these features due to tracking variation. In addition, it also provides the benefit of much less space required on an absorbent article production line, which increasingly becomes premium for productivity perspectives.

Figure 1B:
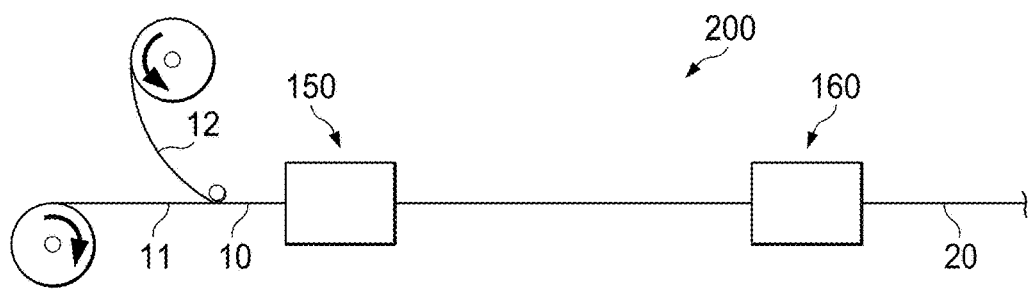
FIG. 1B is a schematic side view of another embodiment of a method and apparatus for deforming a web according to the present invention.

FIGS. 1A and 1B show non-limiting embodiments of a process of the present invention and an apparatus that can be used in the process. In FIGS. 1A and 1B, the machine direction is from left to right. Process 100 carried out according to the example in FIG. 1A comprises providing a precursor web 10 to a weakening unit 150 to weaken the precursor web 10 at a plurality of locations to create a plurality of weakened, melt-stabilized locations in the precursor web 10. Process 200 carried out according to the example in FIG. 1B comprises supplying a first layer 11, and then supplying a second layer 12 onto the first layer 11 to overlap at least part of the first layer 11 to form a precursor web 10. Then, the precursor web 10 is supplied to a forming unit 160 to form a plurality of first features and a plurality of second features on the precursor web 10 simultaneously to provide a deformed web 20.

Figure 2:
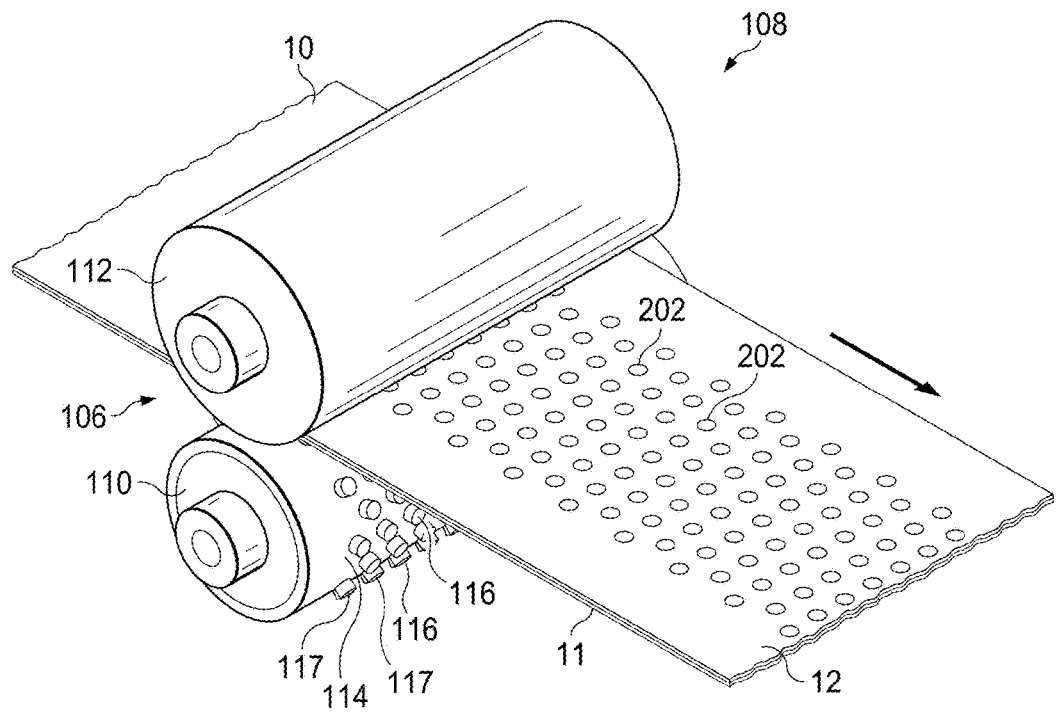
FIG. 2 is a perspective illustration of an exemplary structure of a weakening unit of the process of FIG. 1.
Figure 3:
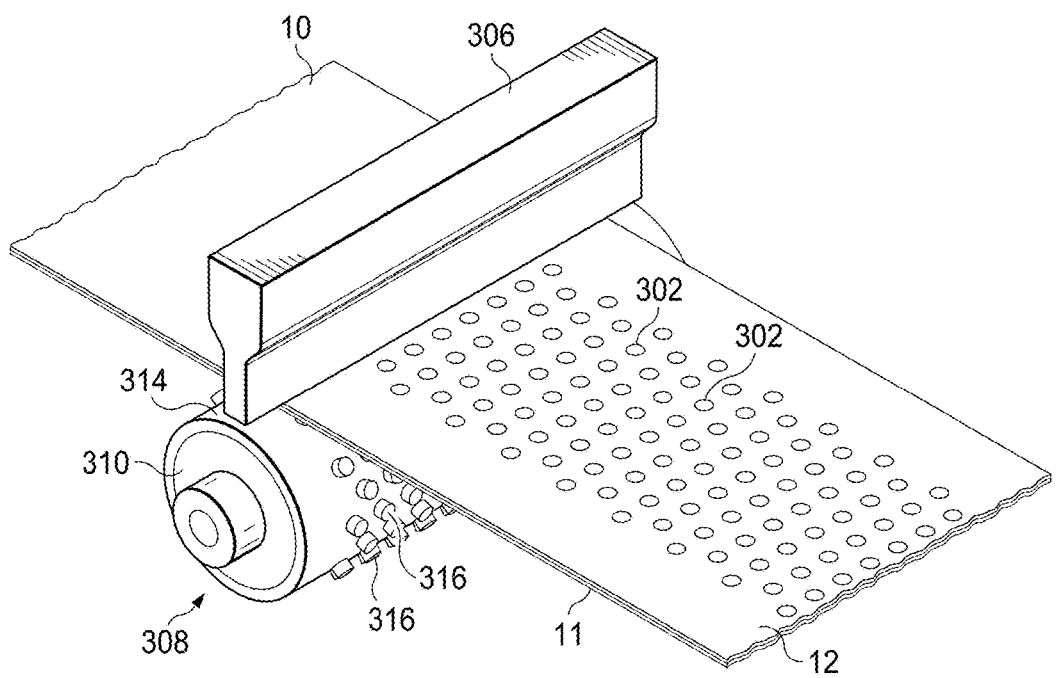
FIG. 3 is a perspective illustration of another exemplary structure of a weakening unit of the process of FIG. 1.

FIGS. 2 and 3 are exemplary structures of the weakening unit 150 in FIGS. 1A and 1B.

Figure 1C:
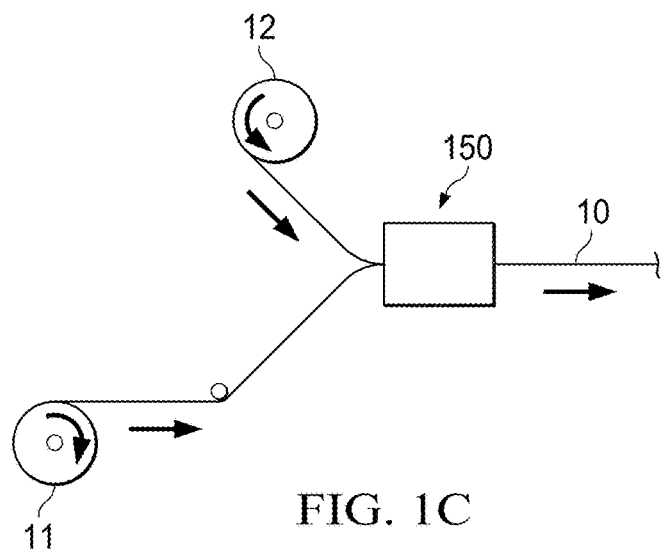
FIG. 1C is a schematic representation of another means of supplying a precursor web in a process of the present invention.

Referring to FIGS. 1A and 2, a precursor web 10 travels and passes through a nip 106 of a web weakening roll arrangement 108 formed by rolls 110 and 112. Alternatively, referring to FIGS. 1B and 2, a first layer 11 is supplied, and then a second layer 12 is supplied onto the first layer 11 to overlap at least part of the first layer 11 to form a precursor web 10 before the precursor web 10 passes through the nip 106. Though the process shown in FIG. 1B indicates introducing the second layer 12 onto the first layer 11 to form a precursor web 10 and feeding the precursor web 10 into the forming unit 160 are carried out sequentially, these two steps can be carried out simultaneously as shown in FIG. 1C. The web weakening roll arrangement 108 preferably comprises a patterned calendar roll 110 and a smooth anvil roll 112. One or both of the patterned calendar roll 110 and the smooth anvil roll 112 may be heated and the pressure between the two rolls may be adjusted by well known means to provide the desired temperature, if any, and pressure to concurrently weaken and melt-stabilize the precursor web 10 at a plurality of locations.

The patterned calendar roll 110 is configured to have a circular cylindrical surface 114, and a plurality of protuberances or pattern elements 116 which extend outwardly from surface 114. The protuberances 116 are disposed in a predetermined pattern with each protuberance 116 being configured and disposed to precipitate a weakened, melt-stabilized location 202 in the precursor web 10 to effect a predetermined pattern of weakened, melt-stabilized locations in the precursor web 10. As shown in FIG. 2, repeating pattern of protuberances 116 may extend around a portion, or portions of the circumference of surface 114 of the calendar roll 110. Alternatively, the protuberances 116 may extend about the entire circumference of the surface 114.

The protuberances 116 are preferably rectangular shape cross sections which extend radially outwardly from surface 114 and which have elliptical distal end surfaces 117 although it is not intended to thereby limit the scope of the present invention to protuberances of only this configuration. Other suitable shapes for distal ends 117 include, but are not limited to circular, square, rectangular, etc. The roll 110 is finished so that all of the end surfaces 117 lie in an imaginary right circular cylinder which is coaxial with respect to the axis of rotation of roll 110.

Protuberances 116 are disposed in a regular predetermined pattern of rows and columns in the embodiment shown in FIG. 2, although it is not intended to thereby limit the scope of the present invention to the pattern of protuberances of only this configuration. The protuberances may be disposed in any predetermined pattern about patterned calendar roll 110.

Anvil roll 112 is preferably a smooth surfaced, right circular cylinder of steel.

Another example of a weakening structure of the weakening unit 150 of process 100 or 200 of FIGS. 1A and 1B is shown in FIG. 3. Referring to FIG. 3, weakening arrangement 308 preferably comprises an ultrasonic transducer 306 and a cylinder 310. As the precursor web 10 is forwarded between the ultrasonic transducer 306 and the anvil cylinder 310, the precursor web 10 is subjected to ultrasonic vibrational energy whereupon predetermined pattern locations of the precursor web 10 are weakened and melt-stabilized.

Anvil cylinder 310 has a multiplicity of discrete pattern protuberances which are generally designated 316 disposed on its outwardly facing surface 314 in a predetermined pattern which extends about the entire circumference of the anvil cylinder. The protuberances 316 can be disposed in a predetermined pattern with each protuberance 316 being configured and disposed to precipitate a weakened, melt-stabilized location 302 in the precursor web 10 to effect a predetermined pattern of weakened, melt-stabilized locations in the precursor web 10. Anvil 310 can have a repeating pattern of protuberances 316 which extend around a portion, or portions of the circumference of surface 314. Alternatively, the protuberances 316 may extend about the entire circumference of surface 314.

Descriptions provided regarding protuberances 116 are applied to protuberances 316. Anvil 310 is finished so that all of the end surfaces lie in an imaginary right circular cylinder which is coaxial with respect to the axis of rotation of anvil cylinder 310.

After having passed through the weakening unit 150, prior to being introduced to forming unit 160, the precursor web 10 includes a plurality of weakened, melt-stabilized locations 202, 302 which generally correspond to the pattern of protuberances 116, 316, respectively.

Referring to FIGS. 1A and 1B, after having passed through the weakening unit 150, the precursor web 10 is fed into the forming unit 160.

The first layer 11 may have a longer width than a width of the second layer 12 in CD, and thus the precursor web 10 comprising the first layer 11 and the second layer 12 may have at least one area, for example one side of the precursor web 10 in MD where the second layer 12 does not exist.

Referring to FIGS. 1A and 1B, the precursor web 10 is supplied to a forming unit 160 where a plurality of first features, a plurality of second features and optional third features and/or fourth features are formed on the precursor web 10 to provide a deformed web 20.

Various processes and apparatuses for deforming webs by forming discrete features on webs known in the art can be utilized to form the first and the second features in the present application.

One type of features preferred for at least one of the first and the second features in the present invention are apertures. Various methods and apparatuses for forming apertures are disclosed in patent literatures. Patents disclosing such methods include: U.S. Pat. Nos. 8,241,543, 3,355,974; 2,748,863 and 4,272,473 disclosing aperture forming methods using apparatus having heated aperture forming elements; and U.S. Pat. No. 5,628,097 disclosing a method for selectively aperturing a nonwoven web or laminate of a nonwoven web and a polymeric film by weakening the web or the laminate at a plurality of locations.

Another type of features preferred for the second discrete features in the present invention are tufts. In many applications, it is desirable that fibrous webs have a bulky texture and/or softness. As one example, a layered composite comprising a nonwoven layer in which nonwoven fibers protrude, or are partially exposed through a polymer film can be useful as a topsheet in absorbent articles as they provide an absorbent structure in which the nonwoven acts as the conveyor of fluid from one side of the composite to the other. The layered composite can be structured such that the fluid collecting side of the layered composite is a polymer film and nonwoven fibers protrude or are partially exposed through the polymer film to the fluid collecting side of the layered composite. Various methods and apparatuses for forming tufts disclosed in patent literatures. Patents disclosing such methods include: WO 1994/058117, WO 2004/59061, and WO 2010/117636 disclosing a method for making tufts on a web using an apparatus comprising a roll comprising a plurality of ridges and grooves.

Referring to FIGS. 1A and 1B, formation of a plurality of first features and a plurality of second features occurs in formation unit 160, and can be carried out on any suitable apparatus that may comprise any suitable type(s) of forming structure. Suitable types of forming structures include, but are not limited to: a pair of rolls that define a nip therebetween, pairs of plates, belts, etc. Using an apparatus with rolls can be beneficial in the case of continuous processes, particularly those in which the speed of the process is of interest. Although the apparatuses will be described herein for convenience primarily in terms of rolls, it should be understood that the description will be applicable to forming structures that have any other suitable configurations.

The rolls used in the apparatuses and processes described herein are typically generally cylindrical. The term "generally cylindrical", as used herein, encompasses rolls that are not only perfectly cylindrical, but also cylindrical rolls that may have elements on their surface. The term "generally cylindrical" also includes rolls that may have a step-down in diameter, such as on the surface of the roll near the ends of the roll. The rolls are also typically rigid (that is, substantially non-deformable). The term "substantially non-deformable", as used herein, refers to rolls having surfaces (and any elements thereon) that typically do not deform or compress under the conditions used in carrying out the processes described herein. The rolls can be made from any suitable materials including, but not limited to steel, aluminum or rigid plastic. The steel may be made of corrosion resistant and wear resistant steel, such as stainless steel. The rolls may or may not be heated. If heated, consideration of thermal expansion effects must be accommodated according to well known practices to one skilled in the art of thermo-mechanical processes.

The rolls may be meshing, non-meshing, or at least partially intermeshing. The terms "meshing" or "inter-meshing", as used herein, refer to arrangements when the forming elements on one of members of the forming structure (e.g., roll) extend toward the surface of the other forming structure and the forming elements have portions that extend between and below an imaginary plane drawn though the tips of the forming elements on the surface of the other forming structure. The term "non-meshing", as used herein, refers to arrangements when the forming elements on one of the members of the forming structure (e.g., roll) extend toward the surface of the other forming structure, but do not have portions that extend below an imaginary plane drawn through the tips of the forming elements on the surface of the other forming structure. The term "partially intermeshing", as used herein, refers to arrangements when the forming elements on one of the members of the forming structure (e.g., roll) extend toward the surface of the other forming structure and some of the forming elements on the surface of the first roll have portions that extend between and below an imaginary plane drawn through the tips of the forming elements on the surface of the other forming structure, and some of the elements on the surface of the first roll do not extend below an imaginary plane drawn through the tips of the forming elements on the surface of the other forming structure.

The rolls typically rotate in opposite directions (that is, the rolls are counter-rotating). The rolls may rotate at substantially the same speed, or at different speeds. The phrase "substantially the same speed", as used herein, means that there is less than 0.3% difference in the speed. The speed of the rolls is measured in terms of surface or peripheral speed. Typically, when the web comprises polymeric materials, the rolls will rotate at substantially the same speed. If the web comprises cellulosic materials, the rolls may rotate at different speeds. The rolls may rotate at different surface speeds by rotating the rolls at different axial speeds, or by using rolls that have different diameters that rotate at the same axial speeds. The rolls may rotate at substantially the same speed as the speed at which the web is fed through the nip between the rolls; or, they may rotate at a greater speed than the speed at which the web is fed through the nip between the rolls.

The rolls used in the apparatuses and methods described herein are used to mechanically deform portions of the web material or materials. The mechanical deformation process may be used to permanently deform portions of the web and form the types of features in the web described above. The terms "mechanically deform" and "mechanical deformation", as used herein, do not include hydroforming processes.

The rolls may have any suitable type of elements on their surface (or surface configuration). The surface of the individual rolls may, depending on the desired type of mechanical deformation, be provided with forming elements comprising: "male" elements such as discrete projections, or continuous projections such as ridges; "female" elements or recesses such as discrete or continuous voids in the surface of the rolls; or any suitable combination thereof. The female elements may have a bottom surface (which may be referred to as depressions, cavities, or grooves), or they may be in the form of apertures (through holes in the surface of the rolls). In some embodiments, the forming elements on the components (such as the rolls) of the forming structure may comprise the same general type (that is, the opposing components may both have male forming elements thereon, or combinations of male and female elements).

The forming elements may have any suitable shape or configuration. A given forming element can have the same plan view length and width dimensions (such as a forming element with a circular or square shaped plan view). Alternatively, the forming element may have a length that is greater than its width (such as a forming element with a rectangular plan view), in which case, the forming element may have any suitable aspect ratio of its length to its width. Suitable configurations for the forming elements include, but are not limited to: ridges and grooves, teeth having a triangular-shaped side view; columnar shapes; elements having plan view configurations including circular, oval, hour-glass shaped, star shaped, polygonal, and the like, and combinations thereof. Polygonal shapes include, but are not limited to rectangular, triangular, hexagonal, or trapezoidal. The forming elements can have tips that are flat, rounded or sharp. In certain embodiments, the shapes of the female elements may differ from the shapes of any mating male forming elements. In certain embodiments, the female forming elements can be configured to mate with one or more male forming elements.

The forming elements can be of any suitable size and have any suitable spacing. The center-to-center spacings among adjacent forming elements may be the same or different. The center-to-center spacing of the forming elements may range from the scale used for such micro-textured webs up to, or greater than, the examples of the size of the center-to-center spacing of the larger forming elements described herein. Suitable configurations for the forming elements are described below with exemplary forming structures such as ring rolls; SELFing rolls; Micro-SELFing rolls, and RKA rolls; male/female embossing rolls.

Figure 4:
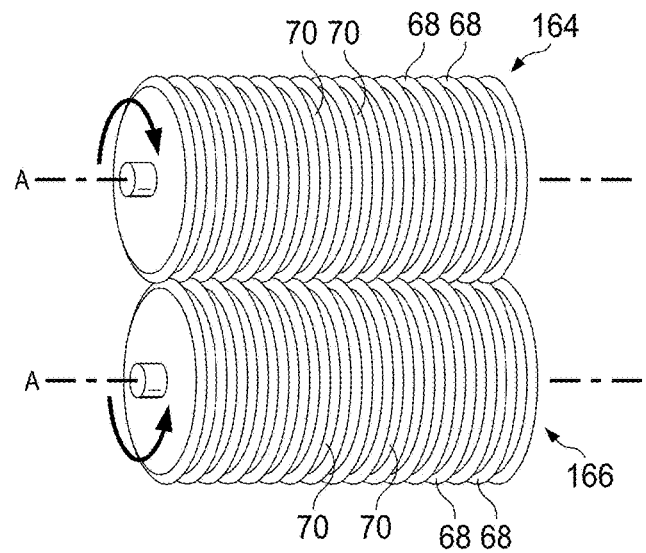
FIG. 4 is a perspective view of a pair of mated forming structures.

FIG. 4 shows an embodiment of forming elements appropriate for ring rolling process. The rolls 164 and 166 are referred to herein as "ring rolls". For ring rolling a web, each surface of rolls 164 and 166 has a plurality of alternating ridges 68 and grooves 70 extending around the circumference of the rolls. In other embodiments, the ridges and grooves may extend parallel to the axes A of the rolls. Referring to FIG. 4, the roll 164 includes a plurality of ridges 68 and corresponding grooves 70 which extend about the entire circumference of roll 164. Roll 166 includes a plurality of ridges 68 and a plurality of corresponding grooves 70. Ridges 68 on roll 164 intermesh with or engage grooves 70 on roll 166, while ridges 68 on roll 166 intermesh with or engage grooves 70 on roll 164.

Figure 5:
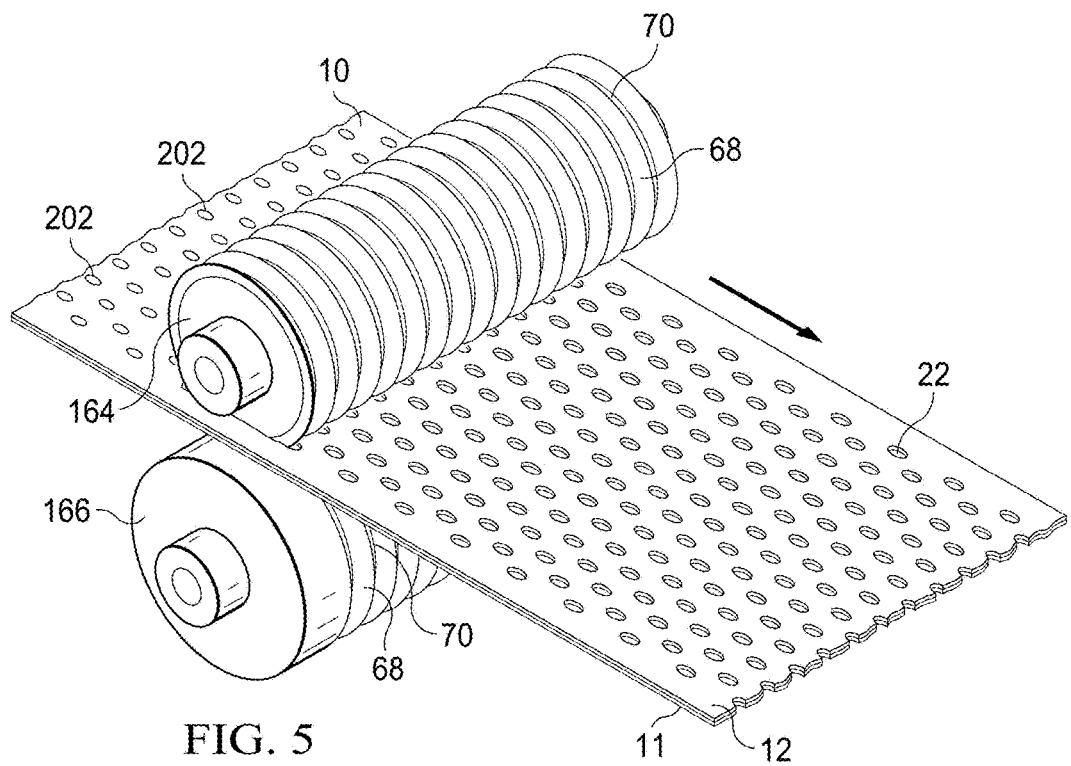
FIG. 5 is a perspective illustration of a process to provide a tensioning force on a web using mated forming structures of FIG. 4.

As shown in FIG. 5, ring rolling can be used as incremental stretching rolls to apply a tensioning force to a precursor web 10 which comprises a first layer 11 and second layer 12 and has weakened, melt-stabilized locations 202 to cause the precursor web 10 to rupture at the plurality of weakened, melt-stabilized locations 202 creating a plurality of apertures 22 in the precursor web 10 coincident with the plurality of weakened, melt-stabilized locations 202. With respect to FIG. 5 or other figures except FIG. 2, weakened, melt-stabilized locations 202 indicate weakened, melt-stabilized locations regardless forming process thereof, and are not limited to weakened, melt-stabilized locations formed by the structure of a weakening unit shown in FIG. 2.

As the precursor web 10 passes through the ring rolls, the precursor web 10 is subjected to tensioning in the cross-machine direction causing the precursor web 10 to be extended in the CD direction. Alternatively, or additionally the precursor web 10 may be tensioned in the machine direction. The tensioning force placed on the precursor web 10 is adjusted such that it causes the weakened, melt-stabilized locations 202 to rupture creating a plurality of apertures 22 coincident with the weakened melt-stabilized locations 202 in the precursor web 10. However, the bonds of the precursor web 10 are preferably strong enough such that they do not rupture during tensioning, thereby maintaining the precursor web 10 in a coherent condition even as the weakened, melt-stabilized locations rupture. However, it may be desirable to have some of the bonds rupture during tensioning. Other exemplary structures of incremental stretching mechanisms suitable for incrementally stretching or tensioning the precursor web 10 are described in International Patent Publication No. WO 95/03765.

Figure 6:
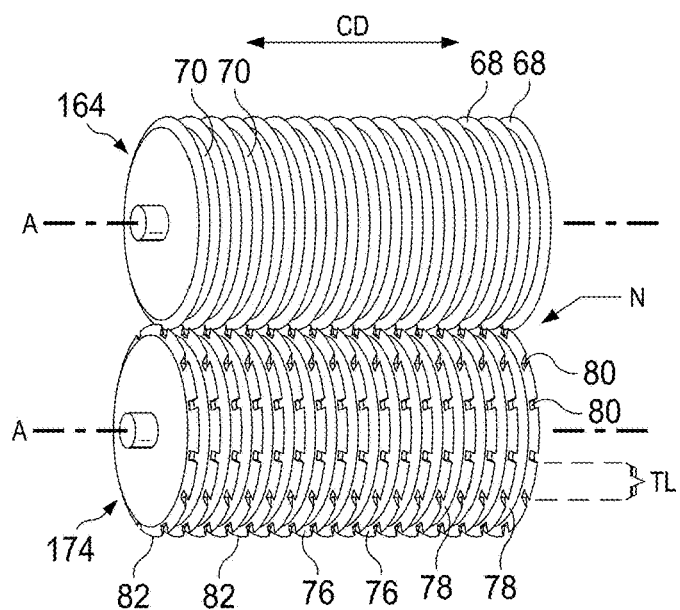
FIG. 6 is a perspective view of another pair of mated forming structures.

FIG. 6 shows a forming elements embodiment appropriate to form tufts or rib-like structures suitable for use in the processes and apparatuses described herein. In FIG. 6, the top roll 164 is a ring roll having circumferential ridges 68 and grooves 70 as described with respect to FIG. 5, and the bottom roll 174 has forming elements which The Procter & Gamble Company's "SELF" or "SELFing" rolls have. The forming elements on the SELF rolls, that is SELF teeth, can be oriented in either the machine direction (MD) or the cross-machine direction (CD). In the embodiment shown in FIG. 6, the SELF roll 174 comprises a plurality of alternating circumferential ridges 76 and grooves 78. The ridges 76 have spaced apart channels 80 formed therein that are oriented parallel to the axis A of the roll. The channels 80 form breaks in the ridges 76 that create discrete forming elements or teeth 82 on the SELF roll 174. Forming elements, the teeth 82, have their longer dimension oriented in the MD. The SELF configuration shown in FIG. 6 will be referred to herein as a standard "CD SELF" since the teeth are aligned in rows in the MD and CD, and in the usual SELF process, the material being fed into the nip N having such a SELF configuration would be stretched in the CD.

In other embodiments, which are described in the SELF patents that are incorporated by reference herein, the SELF roll can comprise a machine direction, or "MD SELF" roll. Such a roll will have alternating ridges and grooves that are oriented parallel to the axis A of the roll. The ridges in such a roll have spaced apart channels formed therein that are oriented around the circumference of the roll. The channels form breaks in the ridges to form discrete forming elements or teeth on the MD SELF roll. In the case of MD SELF rolls, the teeth have their longer dimension oriented in the CD.

Figure 7A:
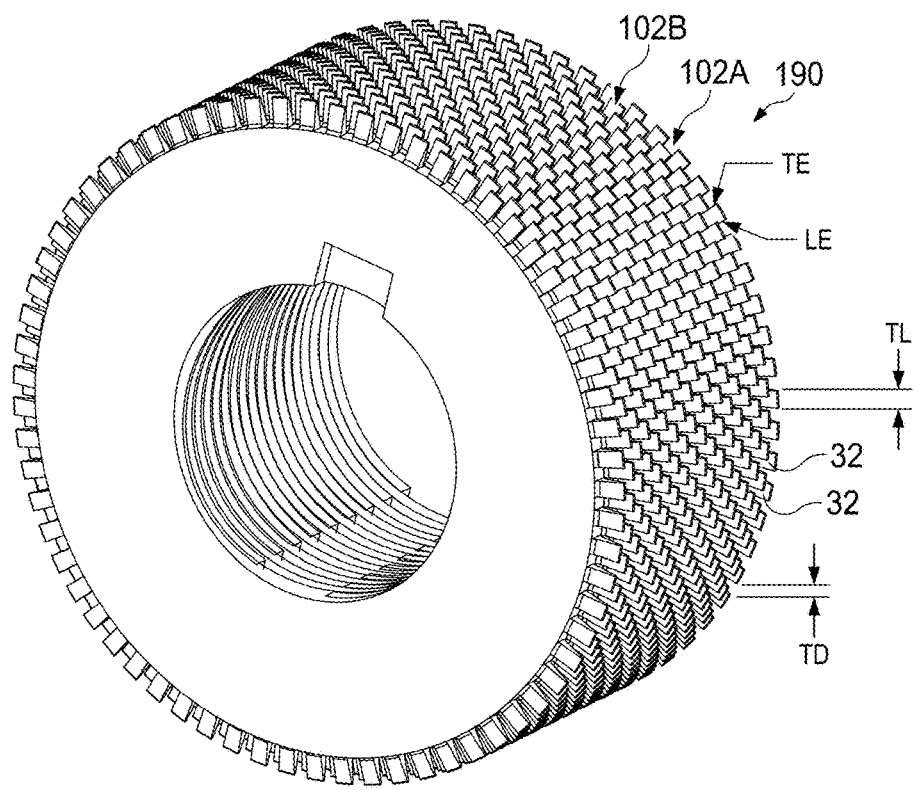
FIG. 7A is an enlarged perspective view of a CD SELF roll with a staggered pattern of teeth thereon.

FIG. 7A shows another embodiment of forming elements to form tufts or tuft like features suitable for use in the processes and apparatuses described herein. In this embodiment, the roll 190 comprises a variation of one of The Procter & Gamble Company's CD SELF rolls. As shown in FIG. 7A, the surface of the roll has a plurality of spaced apart teeth 32. The teeth 32 are arranged in a staggered pattern.

More specifically, the teeth 32 are arranged in a plurality of circumferentially-extending, axially-spaced rows, such as 102A and 102B, around the roll. But for the spacing TD between the teeth in each row, the teeth in each roll would form a plurality of circumferentially-extending, axially-spaced alternating ridges and grooved regions. The tooth length TL and machine direction spacing TD can be defined such that the teeth in adjacent rows 102A and 102B either overlap or do not appear to overlap when the rolls are viewed from one of their ends. In the embodiment shown in FIG. 7A, the teeth 32 in adjacent rows are circumferentially offset by a distance of about 0.5x (where "x" is equal to the tooth length TL plus the MD spacing TD between teeth in a given row). In other words, the leading edges LE of adjacent teeth in adjacent rows will be offset in the MD by about 0.5x.

The roll 190 can be aligned with an opposing roll which has ridges and grooves therein so that the rows of teeth in one roll align with the grooved regions between the teeth in the opposing roll. The staggered tooth pattern allows the precursor web 10 to be mechanically impacted to form features in a staggered pattern.

Figure 7B:
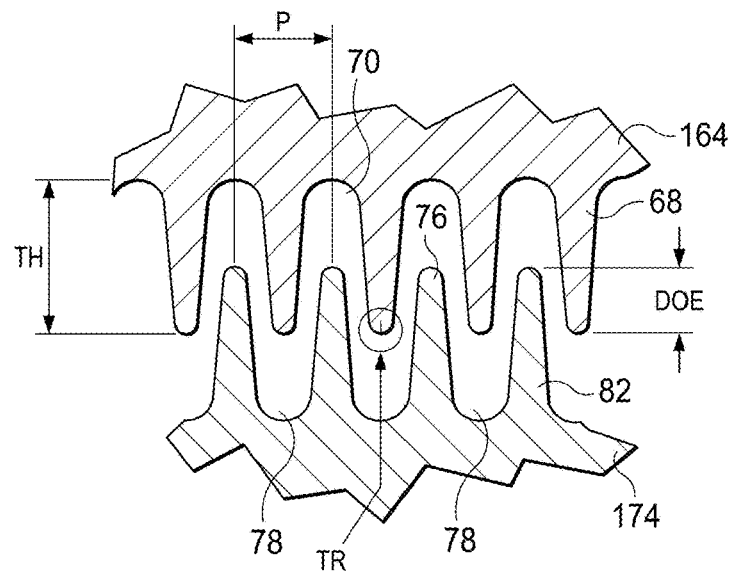
FIG. 7B is a cross-section of a portion of the mated forming structures shown in FIG. 6.

FIG. 7B shows in cross section a portion of the intermeshing rolls 166 and 174 shown in FIG. 6 including teeth 82 which appear as ridges 76 and grooves 78 between the teeth 82. The teeth can have a triangular or inverted V-shape when viewed in cross-section. The vertices of teeth are outermost with respect to the surface of the rolls. As shown in FIGS. 7A and 7B, teeth 82 that have a tooth height TH, a tooth length TL, and a tooth-to-tooth spacing (or ridge-to-ridge spacing) referred to as the pitch P. For staggered rolls, the pitch is equal to the spacing between adjacent rows of forming elements. The tooth length TL in such embodiments is a circumferential measurement. The outermost tips of the teeth have sides that are preferably rounded to avoid cuts or tears in the precursor material. The size and shape of the tooth tip may be specified via the tip radius TR. The leading and trailing edges of the teeth may have a radius as well, or the teeth may form a right angle (and have no radius). As shown, the ridges 68 of one roll extend partially into the grooves 78 of the opposed roll to define a "depth of engagement" DOE, which is a measure of the level of intermeshing of rolls 164 and 174. The depth of engagement can be zero, positive for meshing rolls, or negative for non-meshing rolls. The depth of engagement DOE, tooth height TH, tooth length TL, tooth spacing TD, tip radius TR, and pitch P can be varied as desired depending on the properties of precursor web 10 and the desired characteristics of a deformed web from the precursor web 10.

The teeth can have any suitable dimensions. In certain embodiments of the SELF rolls, the teeth can have a length TL ranging from about 0.5 mm (0.020 inches) to about 13 mm (0.512 inches) and a spacing TD from about 0.5 mm to about 13 mm, a tooth height TH ranging from about 0.5 mm to about 17 mm (0.669 inches), a tooth tip radius TR ranging from about 0.05 mm (0.002 inches) to about 0.5 mm (0.020 inches), and a pitch P between about 1 mm (0.040 inches) and 10 mm (0.400 inches). The depth of engagement E can be from about −1 mm to about 16 mm (up to a maximum approaching the tooth height TH). Of course, E, P, TH, TD, TL, and TR can each be varied independently of each other to achieve the desired properties in the web.

Figure 7C:
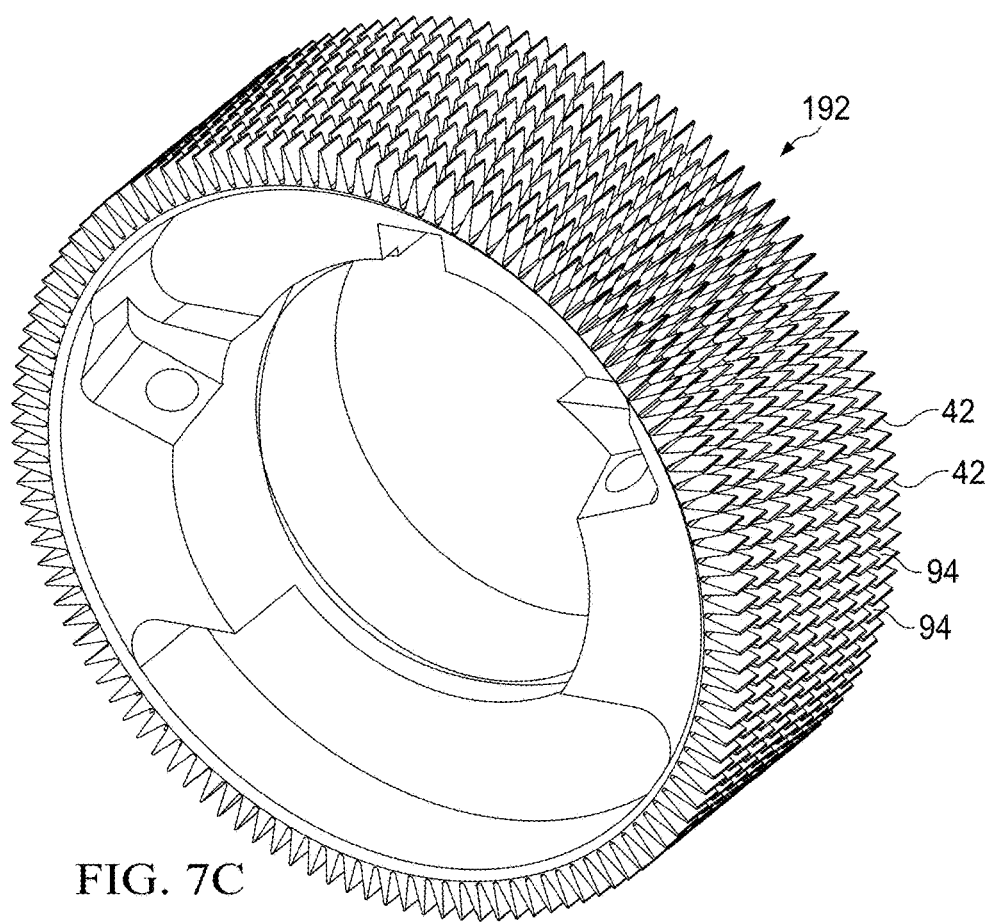
FIG. 7C is an enlarged perspective view of a MD SELF roll with a staggered pattern of teeth thereon.

FIG. 7C shows an alternative forming elements embodiment appropriate to form tufts or rib-like structures suitable for use in the processes and apparatuses described herein. The roll 192 is referred to herein as an "MD staggered SELF" roll in which the teeth 42 are oriented with their longer dimension oriented in the CD and are staggered. The roll 192 has circumferentially extending channels 94 formed between the teeth.

Figure 8:
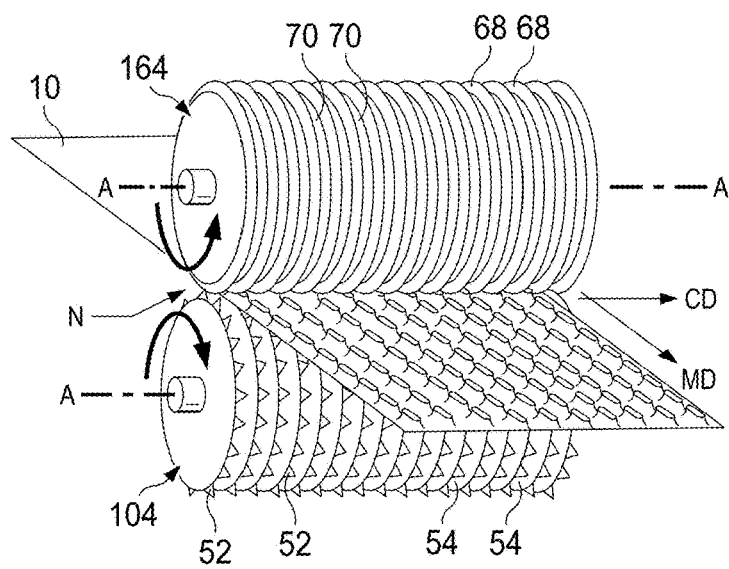
FIG. 8 is a perspective view of another pair of mated forming structures.

FIG. 8 shows an alternative forming elements embodiment to form apertures suitable for use in the processes and apparatuses described herein. In FIG. 8 the top roll 164 is a ring roll, and the bottom roll 104 is referred to herein as a Rotary Knife Aperturing (or "RKA") roll. As shown in FIG. 8, the rolls comprise a pair of counter-rotating, intermeshing rolls, wherein the top roll 164 comprises circumferentially-extending ridges 68 and grooves 70, and the bottom roll 104 comprises pyramid shaped teeth 52 with at least six sides, the sides being substantially triangular and being tapered from a base to a tip. The teeth 52 are arranged in spaced apart circumferential rows with grooves 54 therebetween. The teeth 52 are joined to the bottom roll 104 at the base, and the base of the tooth has a cross-sectional length dimension greater than a cross-sectional width dimension. Typically, apertures are formed in the precursor web 11 as the teeth 52 on the RKA roll 104 intermesh with grooves 70 on the other roll 164. With respect to tooth height, tooth spacing, pitch, depth of engagement, and other processing parameters, RKA and the RKA apparatus can be the same as described herein with respect to SELF or Micro-SELF. RKA rolls are described in greater detail in U.S. Patent Application Publication No. US 2006/0087053 A1.

Figure 9:
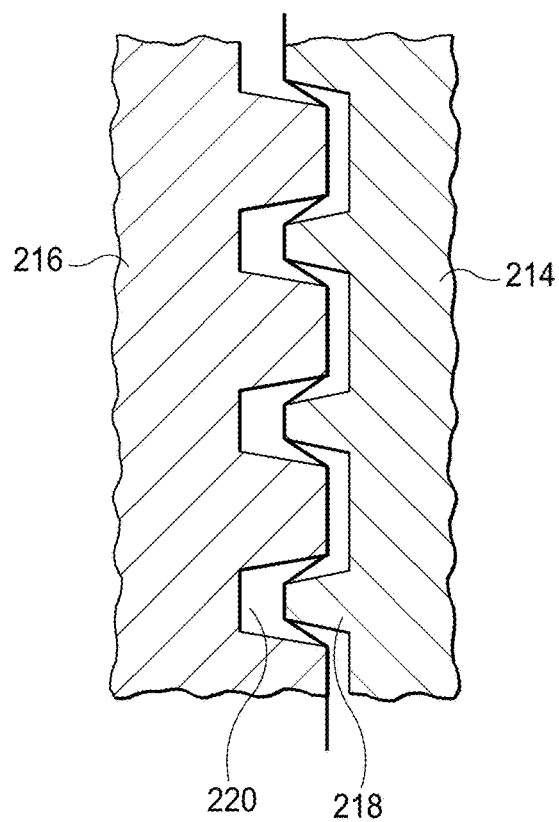
FIG. 9 is a fragmented cross-sectional view through a portion of the nip between a pair of rolls having forming elements to form embossing suitable for the processes and apparatuses.

FIG. 9 shows a portion of the nip between a pair of rolls having an alternative forming elements to form embossing for use in the processes and apparatuses described herein. As shown in FIG. 9, male/female embossing apparatus comprises at least a first and a second patterned roll 214 and 216. The first patterned roll 214 has a male embossing pattern, comprising one or more projections 218 which may be discrete elements (e.g., dot and/or line) embossing elements. The second patterned roll 216 has a female embossing pattern comprising one or more recesses 220, which may be discrete (e.g., dot and/or line configured recesses), into which one or more of the projections of the first patterned roll mesh. The rolls may have matched or unmatched patterns. The elements on the rolls can be of any suitable size and shape. When the embossing rolls have unmatched embossing patterns, they were engraved independently from each other. The rolls 214 and 216 in such an embodiment have enlarged sidewall clearances between adjacent, interengaged projections 218 and recesses 220 of the embossing patterns.

Figure 10:
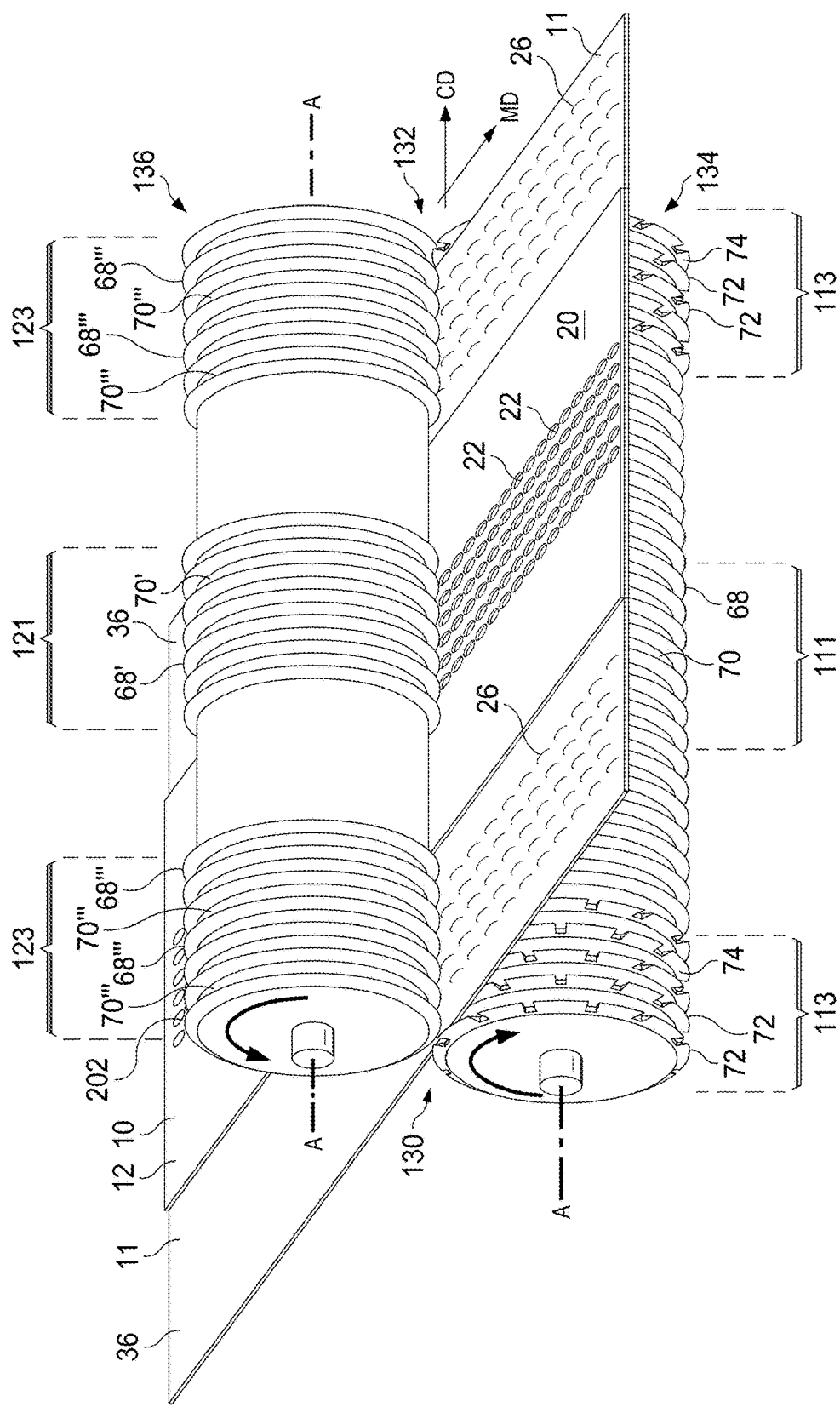
FIG. 10 is a perspective view of a forming structure in accordance with the present invention.

FIG. 10 shows a forming structure 132 as an exemplary forming unit 160 for making a deformed web 20 according to the present invention. Forming structure 132 can provide a deformed web 20 having a plurality of first features (apertures in this case) throughout both the first and second layers and a plurality of second features (tufts or rib-like structures in this case) in the first layer. Precursor web 10 comprising a first layer 11 and a second layer 12 has a plurality of weakened, melt-stabilized locations 202 in at least one predetermined area, a first area.

The forming structure 132 comprises a pair of rolls 134 and 136 having a nip 130, each rotating about parallel axes A.

A first roll 134 comprises a first region 111 comprising a plurality of circumferentially-extending ridges 68 separated by grooves 70, and two second regions 113 comprising a plurality of second forming elements, teeth 72 in this case, separated by grooves 74 on its surface. The first forming elements apply a tensioning force to the precursor web 10 to cause the precursor 10 to rupture at the plurality of weakened, melt-stabilized locations creating a plurality of apertures in the precursor web 10 coincident with the plurality of weakened, melt-stabilized locations.

A second roll 136 comprises a first region 121 having circumferentially-extending ridges 68' separated by grooves 70', ring roll elements; and two second regions 123 comprising a plurality of circumferentially-extending ridges 68''' separated by grooves 70''' on its surface. In one embodiment, the second roll 136 is a ring roll having ring roll elements on its substantially entire surface. The ridges 68' and grooves 70' in the first region 121 of the roll 136 may or may not have the same dimensions as the ridges 68''' and grooves 70''' in the second region 123 of the roll 136. In one embodiment, the second roll 136 has a longer roll diameter in the second region than in the first region. This type of roll design is preferred especially when the first layer 11 is a polymeric film layer.

At least some of ridges 68' and grooves 70' in the first region 121 of roll 136 and at least some of ridges 68 and grooves 70 in the first region 111 of roll 134 are intermeshed, and incrementally stretch precursor web 10 to form apertures 22 in the precursor web 10 coincident with a plurality of weakened, melt-stabilized locations 202. The ridges 68 and grooves 70 in the first region 111 of the roll 134 may have the same dimensions as the ridges 68' and grooves 70' in the first region 121 of the roll 136 as well known in the art of "ring-rolling". Of course, precursor web 10 has melt-weakened locations 202 formed therein prior to precursor 10 entering the nip 130 of forming structure 132. In addition, at least some of the second forming elements in the first roll 134, teeth 72 in FIG. 10, extend inward toward the axis of the second roll 136 beyond at least some of the ridges 68''' in the second region of the second roll 136 to form the plurality of second features. That is, at least some of grooves 70''' of roll 136 are intermeshed with at least some of teeth 72 of roll 134 to form the tufts or rib-like structures 26 in the precursor web 10. The second forming elements, teeth 72 are explained further in FIG. 14B and FIG. 15 later.

In addition, at least some of ridges 68'' of roll 134 are intermeshed with at least some of the grooves 64 of roll 136 to form tufts in the precursor web 10.

In a non-limiting example, the first layer 11 is a polymer film layer and the second layer 12 is a nonwoven layer. In another non-limiting example, both the first layer 11 and the second layer 12 are nonwoven layers.

The process according to the present invention, the first features are formed through both the first and second layer in z-dimension and the second features by the second forming elements such as teeth 72 in FIG. 10 are formed in an area of a web where the second layer does not exist.

In FIG. 10, at least one of roll 134 or 136 may further comprise additional forming elements (not indicated in FIG. 10) to form additional features on precursor web 10. The additional forming elements may be located in a region separate from either the first region or the second region of roll 134 or 136. At least some of the additional forming elements may be located in a first region in roll 134 or 136 resulting additional features intermixed with the first features.

In one embodiment, the second forming elements can, for example, comprise standard or staggered CD SELF teeth or MD SELF teeth, RKA teeth such as shown in FIG. 8, another raised ridge RKA teeth, raised ridge SELF teeth disclosed in WO 2012/149074A, or standard or staggered IPS teeth disclosed in U.S. Pat. No. 7,648,752.

In the particular embodiment shown in FIG. 10, the second forming elements 72 of roll 134 are staggered CD SELF teeth or CD IPS teeth and applied in an area of a precursor web 10 where the second layer 12 does not exist. The tips of at least some of the second forming elements 72 of roll 134 extend inward toward the axis of the roll 136 to a depth beyond the top of at least some of the ridges 68''' on the roll 136.

One advantage of the process and/or apparatus described above is that the deformed web can be produced in-line with other production equipment on a manufacturing line for producing disposable absorbent articles. For example, a process or an apparatus such as the weakening unit 150 or the forming unit 160 shown in FIG. 1A or 1B can be inserted as a unit operation into an existing manufacturing line. As unit operations themselves, such apparatuses can be modular such that they can be changed out relatively quickly and easily with other modular unit operations. When used as part of a manufacturing line for sanitary napkins, for example, the constituent rolls need not be much wider than the product itself, thereby providing for relatively quick and easy installation and removal.

Figure 11:
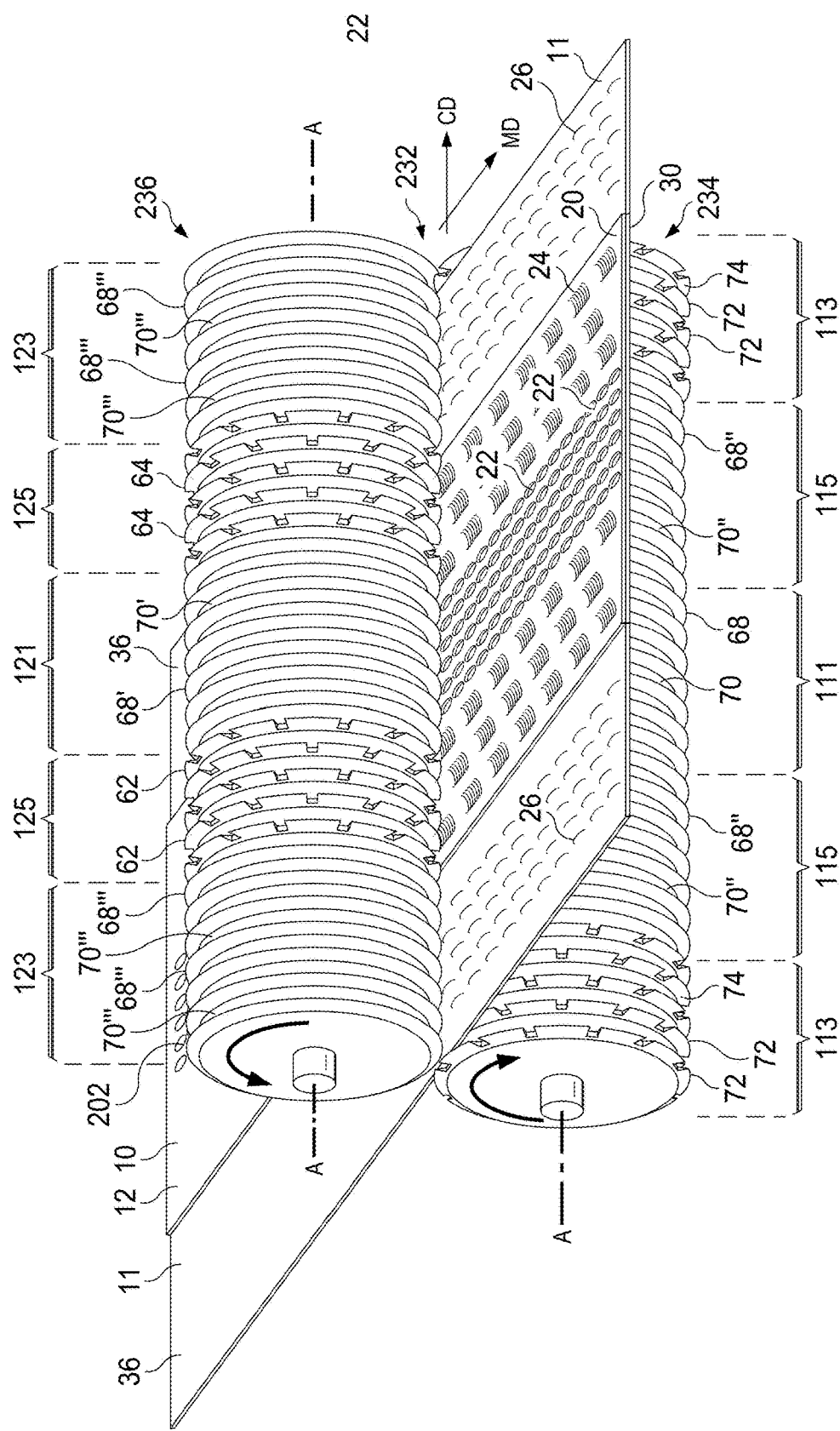
FIG. 11 is a perspective view of another forming structure in accordance with the present invention.

FIG. 11 shows another forming structure 232 as an exemplary forming unit 160 for making a deformed web 20 according to the present invention. The rolls are configured to deform a precursor web 10 with at least three sets of deformations. At least two of the three deformations orient in different directions each other relative to the surface of deformed web 20 that is in z-dimension in the web. The forming structure 232 can provide a deformed web 20 having a plurality of first features (apertures 22 in FIG. 11), a plurality of second features (tufts or rib-like structures 26 in FIG. 11) and a plurality of third (tufts 24 in FIG. 11). Precursor web 10 comprising a first layer 11 and a second layer 12 has a plurality of melt-weakened locations 202 in at least one predetermined area, a first area. Referring to FIG. 11, the forming structure 232 comprises a pair of rolls 234 and 236 having a nip 230, each rotating about parallel axes A. The pair of intermeshing rolls 234 and 236 operates to form the first, second and third features on precursor web 10 simultaneously.

A first roll 234 comprises a first region 111 comprising a plurality of circumferentially-extending ridges 68 separated by grooves 70, ring roll elements, as first forming elements; second regions 113 comprising a plurality of second forming elements, teeth 72 in this case, separated by grooves 74; and third regions 115 comprising a plurality of circumferentially-extending ridges 68'' separated by grooves 70'' on its surface. The circumferentially-extending ridges 68 and grooves 70 in the first region 111 may have the same dimensions as the circumferentially-extending ridges 68'' and grooves 70'' in the third region 115 as well known in the art of "ring-rolling".

A second roll 236 comprises a first region 121 comprising a plurality of circumferentially-extending ridges 68' separated by grooves 70', ring roll elements; two second regions 123 comprising a plurality of circumferentially-extending ridges 68''' separated by grooves 70''', and two third regions 125 comprising ridges having formed therein third forming elements 62, the toothed ridges separated by grooves 64 on its surface. In one embodiment, the second roll 236 has a longer roll diameter in the third than in the first region and/or in the second region. This roll design may be preferred when the first layer 11 is a polymeric film layer.

In one embodiment, the third forming elements can, for example, comprise standard CD SELF teeth, and descriptions for the second forming elements stated with respect to FIG. 10 are applicable for the third forming elements of FIG.

11. Descriptions for the process and apparatus stated with respect to FIG. 10 are applicable for the process and apparatus of FIG. 11.

Referring to FIG. 11, at least one of roll 234 or 236 may further comprise a plurality of fourth forming elements (not indicated in FIG. 11) to form a plurality of fourth features on precursor web 10. The fourth forming elements may be located in a fourth region separate from either the first, second or third region of roll 234 or 236. At least some of the fourth forming elements may be located in a first region or third region in roll 234 resulting a plurality of fourth features intermixed with the first features or third features.

The circumferentially-extending ridges 68 and grooves 70 in the first region 111 may have the same dimensions as the circumferentially-extending ridges 68" and grooves 70" in the second region 113 as well known in the art of "ring-rolling". The circumferentially-extending ridges 68 and grooves 70 in the first region 111 may differ in their dimensions from the circumferentially-extending ridges 68" and grooves 70" in the second region 113.

Obtained deformed web 20 comprising the first layer 11 and the second layer 12 has a first surface 30 comprising the first layer 11 and a plurality of discrete tufts or rib-like structures 24 including fibers integral with and extending from the second layer 12 toward the first layer 11. In case of tufts, each of the tufts 24 has a tuft base proximal to the second layer 12 and a distal portion opposing the tuft base. Tufts may be formed in both layers; or, the tuft of one layer may burst through the other layer as described in greater detail in U.S. Pat. No. 7,648,752. At least part of the distal portion of each of the tufts 24 may be covered by a cap, each cap being an integral extension of the first layer 11 extending over the distal portion of a discrete tuft. Forming capped tufts is described in greater detail in WO 2010/117636.

Referring to FIGS. 10 and 11, in one embodiment, the precursor web 10 and the deformed web 20 comprise an area 36 in outer sides thereof along a machine direction where the second layer 12 does not exist, and the second features (tufts or rib-like structures 26 in FIGS. 10 and 11) are formed. In such an embodiment, at least majority of tufts or rib-like structures 26 may be formed to side areas 36 of the precursor web 10 predetermined to be flaps of a sanitary napkin. In an alternative embodiment, the precursor web 10 and the deformed web 20 comprise the first layer 11 and the second layer 12 in a substantially entire area and the second features are formed through the entire thickness of the precursor web 10.

In another embodiment, at least majority of the plurality of first features are formed in a region of the precursor web 10 predetermined to be a central region of a sanitary napkin.

Figure 12:
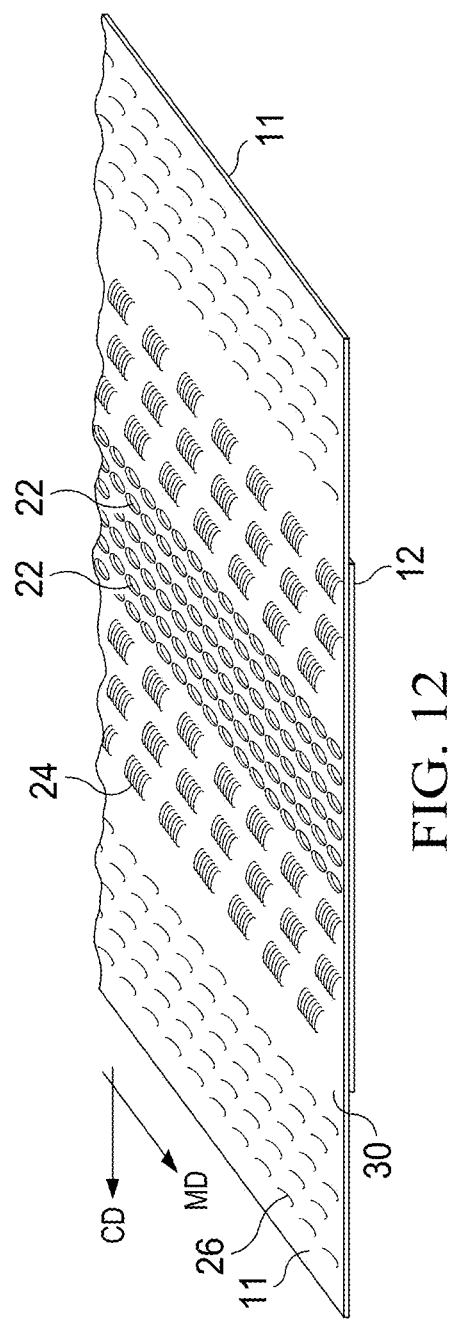
FIG. 12 is a top perspective view of a web that can be produced according to the present process using the forming structure in FIG. 11.

FIG. 12 shows an embodiment of a deformed web 20 made by a process of the present invention using the apparatus shown in FIG. 11, in which the first forming elements are ring roll elements, the second and third forming elements are staggered CD SELF teeth. In FIG. 12, the deformed web 20 comprises a first surface 30 not contacting the second layer, first features comprising a plurality of spaced apart apertures 22 formed throughout the first layer 11 and second layer 12, second features comprising a plurality of spaced apart tufts 24 formed throughout the first layer 11 and second layer 12 towards the first surface 30 of the web 20, and third features comprising a plurality of spaced apart tufts or rib-like structure 26 formed on a first layer towards opposite to the first surface 30. In FIG. 12, the apertures 22, tufts 24, and tufts or rib-like structure 26 may be aligned in rows in the MD.

Figure 13:
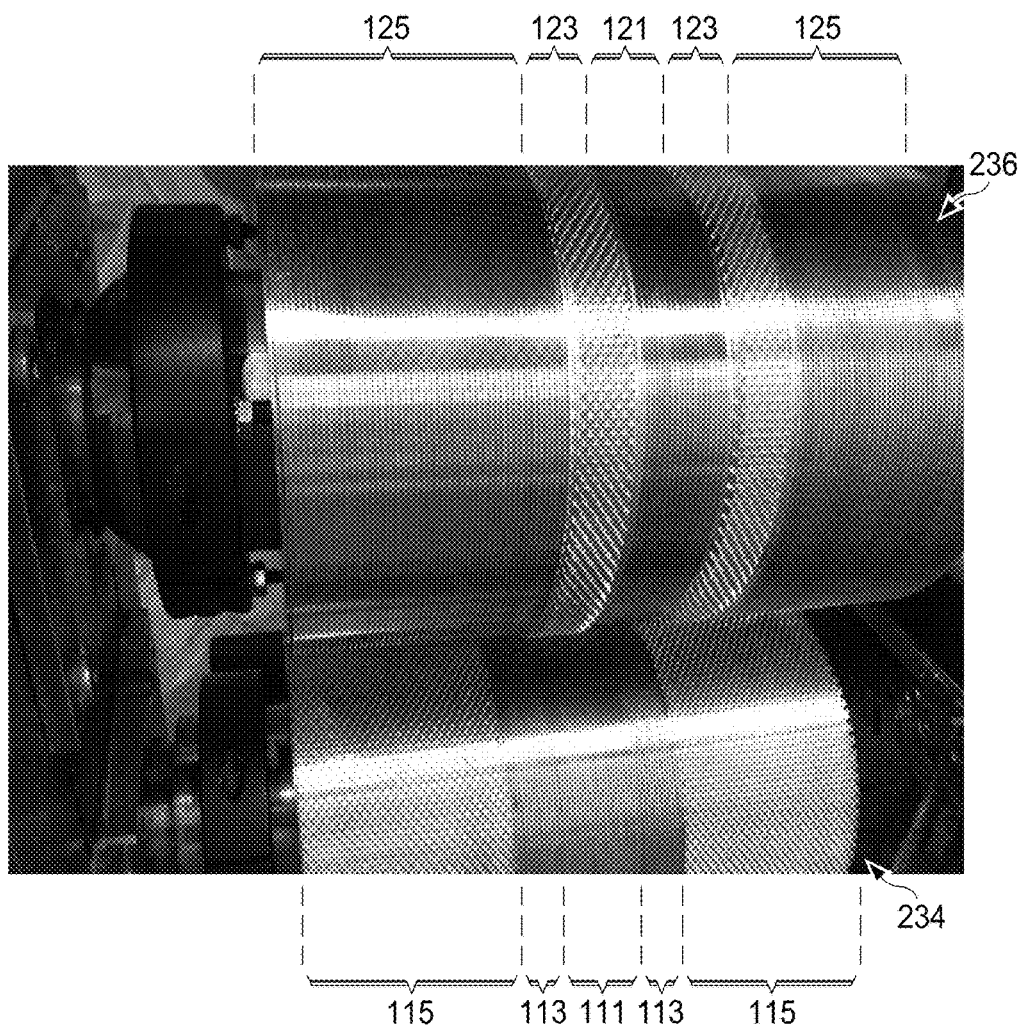
FIG. 13 is a view of intermeshing engagement of portions of the forming structure of FIG. 11.

FIG. 13 is a view of intermeshing engagement of portions of the forming structure of FIG. 11.

Figure 14A:
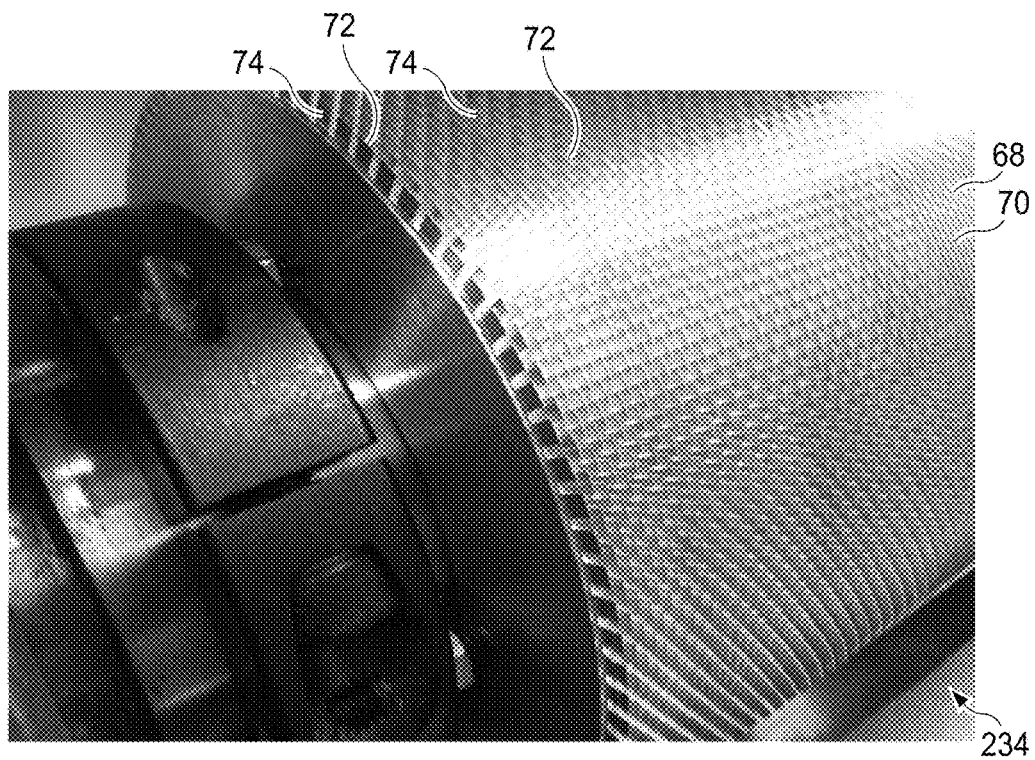
FIG. 14A is a view of a portion of a first roll of the forming structure shown in FIG. 13.
Figure 14B:
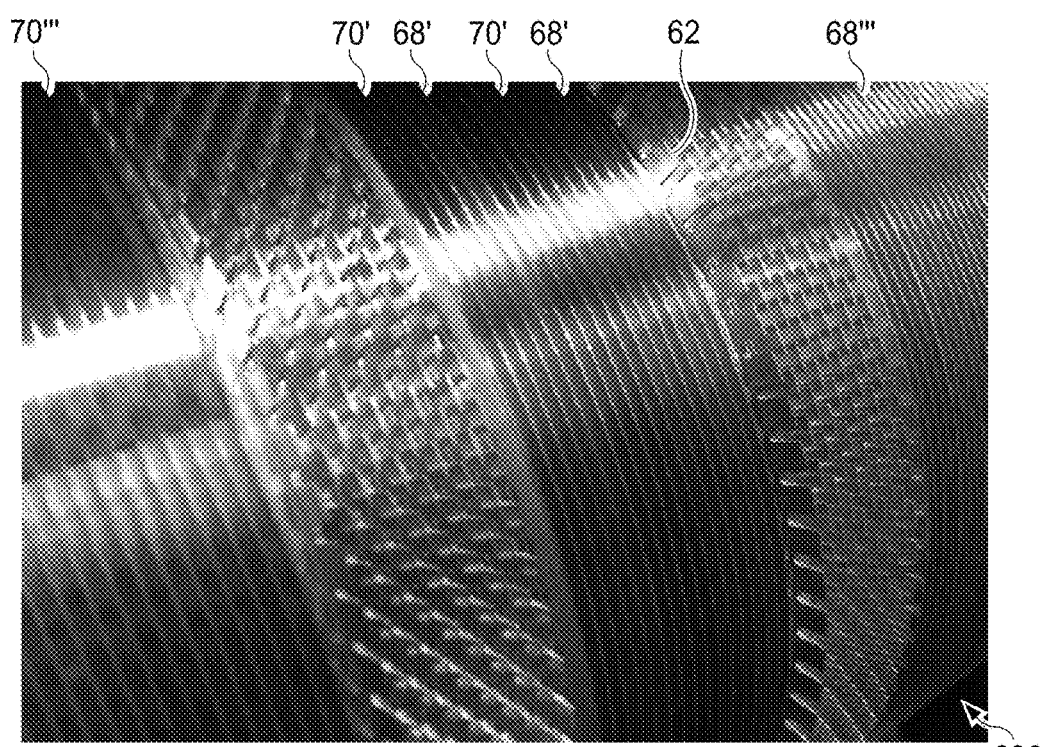
FIG. 14B is a view of a portion of a second roll of the forming structure shown in FIG. 13.

FIG. 14A shows a portion of one embodiment of a first roll 234 where ridges 68 and grooves 70, and teeth 72 separately by grooves 74 as exemplary second forming elements are shown. FIG. 14B shows a portion of one embodiment of a second roll 236 having circumferentially-extending ridges 68', 68'" and grooves 70', 70'", and teeth 62 as an exemplary third forming elements.

Figure 15:
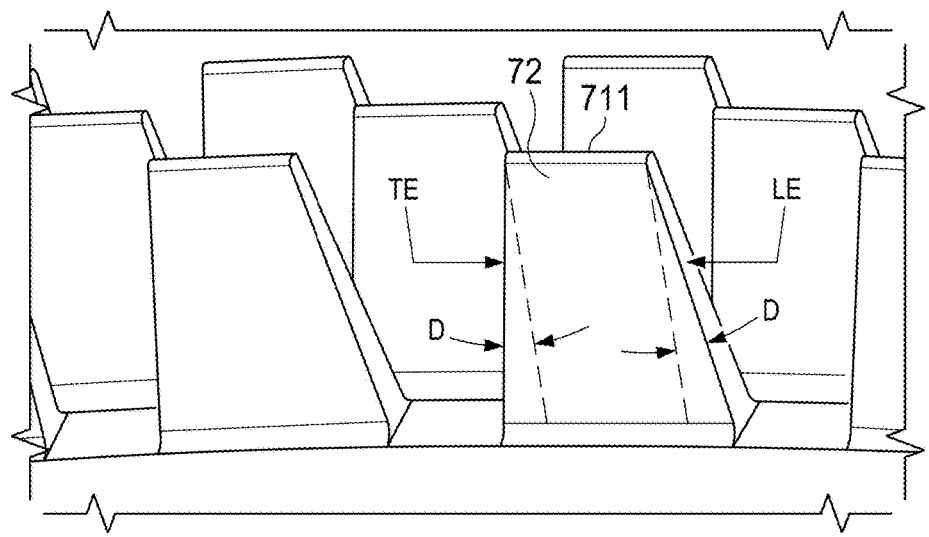
FIG. 15 is a schematic representation of exemplary third forming elements of FIG. 14B.

An enlarged view of the teeth 72 shown in FIG. 14A is shown in FIG. 15. As shown in FIG. 15, each tooth 72 has a tip 711, a leading edge LE and a trailing edge TE. The tooth tip 711 can be rounded to minimize fiber breakage and is preferably elongated. Referring to the apparatus in FIG. 11 and FIG. 15, in one embodiment when the first layer 11 of the precursor web 10 is a polymer film, a deformed web 20 tends to stick to teeth 72 upon being pulled off of roll 234. In order to smoothly pull off the deformed web 20 from roll 234, teeth 72 may have a side wall angle ("D") of in the range of from about 8 to about 14 degrees in at least LE. The side wall angle is an angle the longer sides of the teeth make relative to an imaginary vertical line extending outward from the central axis of the roll through the center of the teeth. Any radius at the tips of the teeth is ignored. LE and TE in the teeth 72 may have the same degree of side wall angle. LE and TE in the teeth 72 may have different degrees of side wall angle.

Figure 16:
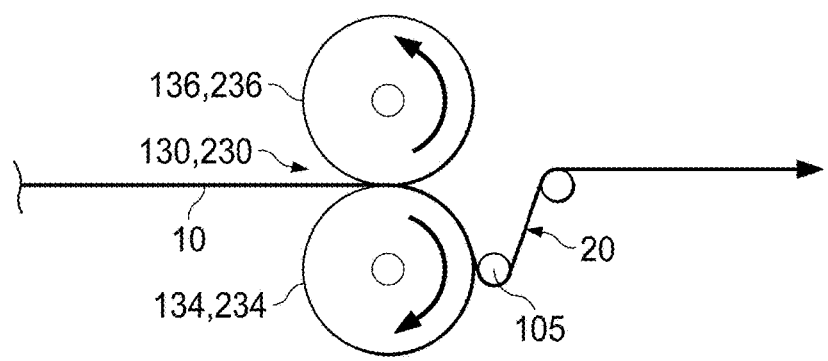
FIG. 16 is a schematic side view of another embodiment of a forming structure in accordance with the present invention.

FIG. 16 is a schematic side view of another embodiment of a forming structure 160 preferable for the present invention. Referring to FIG. 10 or 11, when deformed web 20 tends to stick to second forming elements 72 and/or third forming elements 62 upon being pulled off from rolls 134, and 136 (or 234 and 236), various processing aids can be added as necessary. Formation of the second features in the outer sides a precursor web 10 where only the first layer 11 exists, especially when the first layer 11 is a polymer film, the stickiness issue tends to deteriorate. In one embodiment, as shown in FIG. 16, deformed web 20 exits nip 230 and is directed off of roll 234 over various guide rolls 105 as necessary before being wound for further processing, shipping, or placement for incorporation in a manufactured product. The process of the present invention employs guiding the deformed web 20 to a guide roll 105 which is located in a way that a center of the guide roll and a center of the first roll are in a line substantially parallel to the machine direction. "Substantially parallel to the machine direction" herein means that an imaginary line connecting a center of the guide roll and a center of the first roll, and a machine direction form an angle in the range of from about 0 to about 5 degrees.

The guide roll is placed preferably from about 2 to about 5 mm away from the surface of first roll 234 having third features in each side in machine direction of the roll. If it is placed too far away from first roll 234, it cannot peel the web off as effective. If it is too close from roll 236, there is risk of damaging the guide roll or roll 234. In addition, known various processing aids can be added as necessary. For example, non-stick treatments such as silicone or fluorocarbon treatments can be added. Various lubricants, surfactants or other processing aids can be added to the precursor web 20 or to the rolls 234, 236. Other methods of aiding the removal of the web from the roll include air knives or brushing.

The present invention is also directed to a process for deforming a precursor web by feeding the precursor web in a machine direction into a nip that is formed between two intermeshing rolls. The precursor web comprises a first layer, a second layer, a first area where the first and second layers exist and a second area where the second layer does not exist. The process can form a plurality of first features in the first area of the precursor web and a plurality of second features in the second area of the precursor web simultaneously.

The first roller the rolls having a surface, a circumference and an axis, and comprising a first region comprising a plurality of first forming elements and a second region comprising a plurality of second forming elements on its surface; and the second roll having a surface, a circumference and an axis, and comprising a first region comprising a plurality of circumferentially-extending ridges separated by grooves, and a second region comprising a plurality of circumferentially-extending ridges separated by grooves on its surface. When the precursor web is fed into the nip, at least some of the plurality of first forming elements in the region of the first roll extend inward toward the axis of the second roll beyond at least some of the plurality of circumferentially-extending ridges in the first region of the second roll to form the plurality of first features; and at least some of the second forming elements in the second region of the first roll extend inward toward the axis of the second roll beyond at least some of the plurality of circumferentially-extending ridges in the second region of the second roll to form the plurality of second features.

The first roll may further comprise a third region comprising a plurality of circumferentially-extending ridges separated by grooves on its surface, and the second roll may further comprise a third region comprising a plurality of third forming elements which extend inward toward the axis of the first roll beyond at least some of the plurality of circumferentially-extending ridges in the third region of the first roll to form a plurality of third features.

Each of the first and second and third forming elements can be, for example, comprise standard or staggered CD SELF teeth or MD SELF teeth, RKA teeth such as shown in FIG. 8, another raised ridge RKA teeth, raised ridge SELF teeth disclosed in WO 2012/149074A, or standard or staggered IPS teeth disclosed in U.S. Pat. No. 7,648,752.

The present invention is also directed to an apparatus for deforming a web comprising a first roll and a second roll arranged to form a nip therebetween, wherein the first roll has a surface, a circumference and an axis, and comprises a first region comprising a plurality of first forming elements wherein the plurality of first forming elements comprise a plurality of circumferentially-extending ridges separated by grooves, a second region comprising a plurality of second forming elements, and a third region between the first region and the second region comprising a plurality of circumferentially-extending ridges separated by grooves on its surface; and wherein the second roll has a surface, a circumference and an axis, and comprises a first region comprising a plurality of circumferentially-extending ridges separated by grooves which intermesh with at least some of the plurality of first forming elements in the first roll, a second region comprising a plurality of circumferentially-extending ridges separated by grooves which intermesh with at least some of the second forming elements in the first roll, and a third region comprising a plurality of third forming elements which intermesh at least some of the plurality of circumferentially-extending ridges in the first roll on its surface, wherein the second forming elements comprises teeth, each of the teeth having a leading edge and a trailing end, wherein each of the teeth has a draft angle in the range of from about 8 to about 14 degrees at the leading end.

The present invention is also directed to a process for producing an absorbent article comprising a liquid permeable topsheet comprising a first area, a second area, a plurality of first features formed in the first area and a plurality of second features formed in the second area of the topsheet, and a liquid impermeable backsheet in a continuous matter. The process comprises the steps of: providing a precursor topsheet comprising a first layer and a second layer; weakening the precursor topsheet at a plurality of locations to create a plurality of weakened, melt-stabilized locations in the first area of the precursor topsheet where both the first layer and the second layer exist; forming a plurality of first features and a plurality of second features in the precursor topsheet simultaneously; supplying a precursor backsheet onto the second layer of the precursor topsheet and integrating the precursor topsheet and the precursor backsheet to form an absorbent article assembly; and severing the absorbent article assembly into individual absorbent articles. The plurality of first features is formed coincident with the plurality of weakened, melt-stabilized locations in the first area of the precursor topsheet. The plurality of second features is formed in a second area of the precursor topsheet where the second layer does not exist.

The process for producing an absorbent article according to the present invention may further comprise a step of supplying an absorbent core onto the second layer of the precursor topsheet and integrating the precursor topsheet and the absorbent core prior to supplying an precursor backsheet to form an absorbent article assembly. The process for producing an absorbent article according to the present invention may further comprise a step of supplying a secondary topsheet onto the second layer of the precursor topsheet prior to supplying the optional absorbent core and/or the precursor backsheet to form an absorbent article assembly.

Various methods and apparatuses for producing absorbent articles such as sanitary napkins and diapers known in the art can be utilized to conduct the process of the present invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "90°" is intended to mean "about 90°".

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for deforming a web, the process comprising the steps of:
   a) providing a precursor web comprising a first layer and a second layer, the precursor web having a first surface and a second opposing surface,
   b) weakening the precursor web at a plurality of locations to create a plurality of weakened, melt-stabilized locations in a first area of the precursor web where both the first layer and the second layer exist;
   c) forming a plurality of first features and a plurality of second features and a plurality of third features in the precursor web simultaneously,
   wherein the plurality of first features are formed coincident with the plurality of weakened, melt-stabilized locations in the first area of the precursor web, and
   wherein the plurality of second features are formed in a second area of the precursor web where the second layer does not exist, and wherein the plurality of third features are formed in a third area disposed between the first area and the second area, where the first layer and the second layer exist, wherein the plurality of second features extend in a first direction away from the first surface, wherein the plurality of third features extend in a second direction away from the first surface, and wherein the first direction is opposite the second direction.

2. The process according to claim 1, wherein the precursor web in step b) is weakened by a means selected from a group consisting of heat, pressure and a combination thereof.

3. The process according to claim 1, wherein the plurality of first features are apertures formed by applying a tensioning force to the precursor web to cause the precursor web to rupture at the plurality of weakened, melt-stabilized locations creating a plurality of apertures in the precursor web.

4. The process according to claim 1, wherein majority of the plurality of first features are formed in a region of the precursor web predetermined to be a central region of a sanitary napkin.

5. The process according to claim 1, wherein majority of the plurality of second features are formed in an area of the precursor web predetermined to be flaps of a sanitary napkin.

6. The process according to claim 1, wherein the step c) further forms a plurality of third features in at least one third area of the precursor web where both the first layer and second layer exist simultaneously with forming the plurality of first features and the plurality of second features.

7. The process according to claim 1, wherein the first layer comprises a material selected from a group consisting of a polymeric film, a nonwoven and a combination thereof.

8. The process according to claim 7, wherein the second layer comprises a material selected from a group consisting of a polymeric film, a nonwoven and a combination thereof.

9. The process according to claim 1, wherein at least one of the plurality of first features and the plurality of second features are features selected from the group consisting of apertures, protrusions, depressions, tufts and combinations thereof.

10. The process according to claim 1, wherein the precursor web comprising a first layer and a second layer in step a) is provided by supplying the first layer and supplying the second layer onto the first layer such that the first layer is not overlapped with the second layer in each of outer side of the first layer.

11. The process according to claim 1, wherein the plurality of first features and the plurality of and second features in step c) are formed by feeding the precursor web in a machine direction into a nip that is formed between two intermeshing rolls comprising;
   a first roll having a surface, a circumference and an axis, and comprising a first region comprising a plurality of first forming elements wherein the plurality of first forming elements comprise a plurality of circumferentially-extending ridges separated by grooves, and a second region comprising a plurality of second forming elements on its surface; and
   a second roll having a surface, a circumference and an axis, and comprising a first region comprising a plurality of circumferentially-extending ridges separated by grooves, and a second region comprising a plurality of circumferentially-extending ridges separated by grooves on its surface, and
   when the precursor web is fed into the nip, at least some of the plurality of first forming elements in the first region of the first roll and at least some of the plurality of circumferentially-extending ridges in first region of the second roll are intermeshed to from the plurality of first features, and at least some of the second forming elements in the first roll extend inward toward the axis of the second roll beyond at least some of the plurality of circumferentially-extending ridges in the second region of the second roll to form the plurality of second features.

12. The process according to claim 11, wherein the plurality of second forming elements comprises teeth, each of the teeth having a leading edge and a trailing end, wherein each of the teeth has a draft angle in the range of from about 8 to about 14 degrees at the leading end.

13. The process according to claim 11, wherein the process further comprises guiding the precursor web after step c) to a guide roll which is located in a way that a center of the guide roll and a center of the first roll is in a line substantially parallel to the machine direction.

14. The process according to claim 6, wherein the plurality of first features, the plurality of second features and the plurality of third features in step c) are formed by feeding the precursor web in a machine direction into a nip that is formed between two intermeshing rolls comprising;
   a first roll having a surface, a circumference and an axis, and comprising a first region comprising a plurality of first forming elements wherein the plurality of first forming elements comprise a plurality of circumferentially-extending ridges separated by grooves, a second region comprising a plurality of second forming elements, and a third region comprising a plurality of circumferentially-extending ridges separated by grooves on its surface; and
   a second roll having a surface, a circumference and an axis, and comprising a first region comprising a plurality of circumferentially-extending ridges separated by grooves, and a second region comprising a plurality of circumferentially-extending ridges separated by grooves, and a third region comprising a plurality of third forming elements on its surface, and
   when the precursor web is fed into the nip, at least some of the plurality of first forming elements in the first region of the first roll and at least some of the plurality of circumferentially-extending ridges in first region of the second roll are intermeshed to from the plurality of first features; at least some of the second forming elements in the first roll extend inward toward the axis of the second roll beyond at least some of the plurality of circumferentially-extending ridges in the second region of the second roll to form the plurality of second features; and at least some of the third forming elements in the second roll extend inward toward the axis of the first roll beyond at least some of the plurality of circumferentially-extending ridges in the third region of the first roll to form the plurality of third features.

15. The process according to claim 13, wherein the process further comprises guiding the precursor web after step c) to a guide roll which is located in a way that a center of the guide roll and a center of the first roll is in a line substantially parallel to the machine direction.

16. A process for deforming a multilayer web, the process comprising the steps of:
   a) providing a precursor web comprising a first layer, a second layer, a first area where the first and second layers exist and a second area where the second layer does not exist and a third area disposed between the first area and the second area where the first layer and the second layer exist,
   b) forming a plurality of first features and a plurality of second features and a plurality of third features in the precursor web simultaneously,
wherein the plurality of first features are formed in the first area of the precursor web and the plurality of second features are formed in the second area of the precursor web and the plurality of third features are formed in the third area, by feeding the precursor web in a machine direction into a nip that is formed between two intermeshing rolls comprising;
   a first roll having a surface, a circumference and an axis, and comprising a first region comprising a plurality of first forming elements and a second region comprising a plurality of second forming elements on its surface, and a third region comprising a plurality of third forming elements on its surface; and
   a second roll having a surface, a circumference and an axis, and comprising a first region comprising a plurality of circumferentially-extending ridges separated by grooves, and a second region comprising a plurality of circumferentially-extending ridges separated by grooves on its surface, and
   when the precursor web is fed into the nip, at least some of the plurality of first forming elements in the region of the first roll extend inward toward the axis of the second roll beyond at least some of the plurality of circumferentially-extending ridges in the first region of the second roll to form the plurality of first features; and at least some of the second forming elements in the second region of the first roll extend inward toward the axis of the second roll beyond at least some of the plurality of circumferentially-extending ridges in the second region of the second roll to form the plurality of second features, and wherein the second layer forms a portion of an outer-facing surface on an absorbent article, at least some of the third forming elements in the second roll extend inward toward the axis of the first roll beyond at least some of the plurality of circumferentially-extending ridges in the third region of the first roll to form the plurality of third features.

17. The process according to claim 16, wherein the plurality of second forming elements comprises teeth, each of the teeth having a leading edge and a trailing end, wherein each of the teeth has a draft angle in the range of from about 8 to about 14 degrees at the leading end.

18. The process according to claim 16, wherein the process further comprises guiding the precursor web after step d) to a guide roll which is located in a way that a center of the guide roll and a center of the first roll is in a line substantially parallel to the machine direction.

19. A process for fabricating an absorbent article, the absorbent article comprising a liquid permeable topsheet and a liquid impermeable backsheet, the method comprising the steps of:
   a) providing a precursor topsheet comprising a first layer and a second layer, the precursor topsheet comprising a first surface and an opposing second surface;
   b) weakening the precursor topsheet at a plurality of locations to create a plurality of weakened, melt-stabilized locations in a first area of the precursor topsheet where both the first layer and the second layer exist;
   c) forming a plurality of first features and a plurality of second features and a pluralty of third features in the precursor topsheet simultaneously;
   d) supplying a precursor backsheet onto the second layer of the precursor topsheet and integrating the precursor topsheet and the precursor backsheet to form an absorbent article assembly; and
   e) severing the absorbent article assembly into individual absorbent articles,
   wherein the plurality of first features are formed coincident with the plurality of weakened, melt-stabilized locations in the first area of the precursor topsheet, and
   wherein the plurality of second features are formed in a second area of the precursor topsheet where the second layer does not exist, and
   wherein the plurality of third features are formed in a third area of the precursor topsheet disposed between the second area and the first area, wherein the plurality of third features are created in both the first layer and second layer, wherein the plurality of second features extend in a first direction away from the first surface, wherein the plurality of third features extend in a second direction away from the first surface, and wherein the first direction is opposite the second direction.

20. The process according to claim 19, wherein the steps of a) to e) are carried out in a continuous manner.

* * * * *